United States Patent [19]

Nehra

[11] Patent Number: 5,670,141

[45] Date of Patent: *Sep. 23, 1997

[54] AQUEOUS NITROCELLULOSE COMPOSITIONS

[75] Inventor: Samuel A. Nehra, Grosse Pointe Shores, Mich.

[73] Assignee: Agri-Film, Inc., Grosse Pointe Shores, Mich.

[*] Notice: The term of this patent shall not extend beyond the expiration date of Pat. No. 5,284,885.

[21] Appl. No.: 406,960

[22] PCT Filed: Sep. 28, 1993

[86] PCT No.: PCT/US93/09262

§ 371 Date: Mar. 28, 1995

§ 102(e) Date: Mar. 28, 1995

[87] PCT Pub. No.: WO94/07952

PCT Pub. Date: Apr. 14, 1994

Related U.S. Application Data

[63] Continuation-in-part of Ser. No. 954,723, Sep. 29, 1992, Pat. No. 5,284,885.

[51] Int. Cl.$^6$ .............. A61K 7/043; A61K 7/00
[52] U.S. Cl. ............. 424/61; 424/401; 424/63; 424/488
[58] Field of Search ............ 424/401, 61, 18.03, 424/63, 488

[56] References Cited

U.S. PATENT DOCUMENTS

| | | | |
|---|---|---|---|
| 2,099,501 | 4/1937 | Speicher | 134/79 |
| 2,195,971 | 4/1940 | Peter | 167/85 |
| 3,749,769 | 7/1973 | Sugiyama et al. | 424/61 |
| 3,927,203 | 12/1975 | Seymour et al. | 424/61 |
| 4,126,675 | 11/1978 | Boulogne et al. | 424/61 |
| 4,158,053 | 6/1979 | Greene et al. | 424/61 |
| 4,166,110 | 8/1979 | Isobe et al. | 424/61 |
| 4,384,058 | 5/1983 | Galante | 524/32 |
| 4,421,881 | 12/1983 | Benkendorf et al. | 524/24 |
| 4,495,172 | 1/1985 | Orlowski et al. | 424/61 |
| 4,517,324 | 5/1985 | Lijhmann | 524/27 |
| 4,649,045 | 3/1987 | Gaske et al. | 424/61 |
| 4,798,720 | 1/1989 | Holder | 424/61 |
| 4,814,015 | 3/1989 | Quinlan | 106/170 |
| 4,820,509 | 4/1989 | Yamazaki et al. | 424/61 |
| 4,822,423 | 4/1989 | Soyama et al. | 106/5 |
| 4,897,261 | 1/1990 | Yamazaki et al. | 424/61 |
| 5,093,108 | 3/1992 | Pappas | 424/61 |
| 5,102,654 | 4/1992 | Castrogiovanni et al. | 424/61 |
| 5,130,125 | 7/1992 | Martin et al. | 424/61 |
| 5,284,885 | 2/1994 | Nehra | 524/31 |

FOREIGN PATENT DOCUMENTS 0094041  8/1978  Japan.

OTHER PUBLICATIONS

Hercules Incorporated, CSL-132C "Nitrocellulose Lacquer Emulsions —Preparation and Performance for Improving Paper and Paper Products" (Apr. 1986).

Hercules Incorporated, CSL-142A "Nitrocellulose Improved Water Resistance of Polyvinyl Acetate Coatings" (Apr. 1983).

Hercules Incorporated, CSL-225A "Preparation Procedures for Nitrocellulose Waterborne Coatings and Inks" (Jun. 1983).

Kintish, L., Soap Cosmetics Chemical Specialties, Jul.; 29–31, 52–53, 58–59 (1992).

*Primary Examiner*—Sallie M. Gardner
*Attorney, Agent, or Firm*—Howard & Howard

[57] ABSTRACT

The present invention comprises aqueous cellulose solutions and methods of their making. The solutions of the invention provide coatings and can be employed as nail coatings, protective coatings and non-wax polishes.

9 Claims, No Drawings

AQUEOUS NITROCELLULOSE COMPOSITIONS

RELATED APPLICATION

This application is based on PCT application Ser. No. PCT/US93/09262 filed Sep. 28, 1993, published as WO94/07952 Apr. 14, 1994, which is a continuation-in-part of U.S. application Ser. No. 07/954,723, filed Sep. 29, 1992, now U.S. Pat. No. 5,284,885.

FIELD OF THE INVENTION

The present invention relates generally to aqueous cellulose compositions and, more particularly, to aqueous cellulose-based coatings and methods of making.

BACKGROUND OF THE INVENTION

Nitrocellulose has long been used as a base film forming material for various films and coatings. One of its many applications is in lacquer emulsions used in the manufacture of nail coatings or polishes.

Nitrocellulose emulsions used in coatings are generally obtained through either direct emulsification or indirectly through various inversion techniques. For example, a conventional lacquer of nitrocellulose and solvent with emulsifiers is emulsified with the addition of water, inverting from a water-in-lacquer to a lacquer-in-water emulsion. Another inversion technique begins with water-wet nitrocellulose which is dissolved in the solvent system, with water from the mixture dispersing throughout the solvent phase. Additional water containing an emulsifying agent is added forming a lacquer-in-water emulsion by inversion.

Although many improvements have been made in nail coating performance, conventional nail coatings still employ a relatively high percentage of volatile water-immiscible solvents which are relatively toxic, in order to emulsify the nitrocellulose based material. Water-miscible solvents are not ordinarily used because they promote formation of water-in-lacquer rather than lacquer-in-water emulsions. Due to the high percentage of water-immiscible solvents ordinarily employed to emulsify the nitrocellulose, the resultant coatings are flammable and potentially toxic, with a high rate of volatilization and an unpleasant odor. In addition, some individuals become sensitized and develop reactions to these nail coatings.

It is therefore desirable to provide a method for preparing cellulose solutions with less reliance on a high percentage of harsh solvents. It is also desirable to provide cellulose-based compositions which have reduced environmental impact by employing a greater percentage of water. It is further desirable to provide nitrocellulose-based compositions for coatings with a lower percentage of solvent. It is further desirable to provide improved nail coatings with a lower percentage of solvents, but which do not sacrifice durability and hardness characteristics.

SUMMARY OF THE INVENTION

The present invention provides novel aqueous cellulose compositions and methods of making such compositions. The present invention also encompasses the use of aqueous cellulose compositions in coatings and the method of making. The coating compositions are free-flowing liquids which may be either pigmented or non-pigmented and applied to human nails in a conventional manner. The coating compositions may also be employed as polishes and protective coatings.

The method for preparing cellulose in water, hereinafter "aqueous cellulose solution," generally comprises the steps of mixing solid nitrocellulose, ethylcellulose or cellulose acetate butyrate and a substantial amount of water, adding more water with continued mixing and adding a small amount of solvent with continued mixing. The water and solvent may also be added simultaneously. The above steps are performed at an elevated temperature of about 95° C. to boiling. The resulting mixture is azeotropic-like.

Nitrocellulose-based coatings of the present invention are obtained by mixing a proportional amount of acrylic-based polymers and aqueous nitrocellulose solution. Various additives such as wetting agents, germicides and thickeners may also be added. Pigmented coatings are formed by adding dispersed treated pigments to the nitrocellulose-based coatings. The dispersed treated pigments are obtained by repeatedly mixing the pigments with silanes, and titanates, desiccating and then, milling the treated pigments with a wetting agent and a dispersing surfactant.

The nail coatings of the present invention are primarily aqueous rather than solvent-based and employ generally gentler, low volatile organic solvents. The hardness, durability and water resistance of the nail coatings of the invention are equal to or surpass those of nail coatings presently on the market. The coatings of the present invention are also less affected by humidity than solvent-based coatings. In addition, the coatings of the present invention have a high solid content (28%–43% solids), which affords better coverage of imperfections in the nail. The coatings of the present invention do not appear to form a continuous film as do solvent-based coatings and do not easily chip due to their adhesive and flexible qualities. The decrease in the high percentage of solvents reduces solvent-related problems. The coatings of the present invention also more readily permit the exchange of body fluids with the atmosphere, i.e. allowing the nail bed to "breathe."

The coatings of the present invention may also be used as a polish on vinyl, leather, finished and unfinished wood, formica and flooring, including linoleum, ceramic tile, marble and mineral flooring and the like. The coatings are also useful as polishes for automobiles.

DETAILED DESCRIPTION OF THE PREFERRED EMBODIMENTS

I. Preparation of The Aqueous Cellulose Solution

The aqueous cellulose solution is made with solvents selectively compatible with polymers to which it will be added, to enhance the properties of the particular polymer being used. The invention can include nitrocellulose, ethylcellulose or cellulose acetate butyrate, although it will be appreciated that in alternative embodiments, other suitable cellulose compounds or complexes may be used. Examples of solvents that may be employed in the present invention include but are not limited to propylene glycol monopropyl ether, ethylene glycol monopropyl ether, ethyl 3-ethoxypropionate, isopropyl or ethyl alcohol (32 g) with ethylene glycol monobutyl ether (26 g), dipropylene glycol monobutyl ether, dipropylene glycol methyl ether, propylene glycol methyl acetate, propylene glycol methyl ether acetate, dipropylene glycol methyl ether acetate, isopropyl acetate, N-methyl-2-pyrrolidone, isopropyl or ethyl alcohol and propylene glycol methyl ether. Examples of preferred solvents include propylene glycol monobutyl ether, ethylene glycol monobutyl acetate, ethylene glycol monobutyl ether and diethylene glycol monoethyl ether. The solvents of the present invention may also act as a freeze-thaw factor. The present invention may also employ surfactants including but not limited to El 620, available from RHONE POULENC of Cranbury, N.J., FC129 FLUORAD, available from 3M of St. Paul, Minn., SURFYNOL S-104E, available from Air Products, Inc. of Allentown, Pa., L-7001, available from Union Carbide Corp. of Danbury, Conn., and A-196, available from American Cyanamid. The invention can also include other additives such as ammonium hydroxide, 28%. The pH of the solution is in the range of from about 2.0 to about 6.0.

Nitrocellulose, ethylcellulose and cellulose acetate butyrate (hereinafter referred to generally as "cellulose compounds") were put into aqueous solutions according to the following general technique wherein the amount of distilled water varied from about 2 parts by weight to about 20 parts by weight for every part by weight of cellulose compound (all measurements are based on employing an open vessel in the preparation of the compositions). The nitrocellulose was 80% by weight, water packed. Ethylcellulose and cellulose acetate butyrate were 100% by weight. An example of preferred nitrocellulose is that sold by Aqualon, a Hercules Corporation. An example of preferred ethylcellulose is that sold by Dow Chemical Co. of Midland, Mich. An example of preferred cellulose acetate butyrate is that sold by Eastman Kodak Co. of Rochester, N.Y. The solvents employed range from about 2 parts by weight to about 20 parts by weight for every part by weight of cellulose compound. The surfactants employed vary from about 0.05 g to about 1.0 g without dilution for every part by weight of cellulose compound. The general technique consists of applying heat in the range of from about 70° C. to about boiling, preferably at about 95° C. to about boiling and mixing at a mixer speed of around 8.5 or at a speed great enough to form a vortex in the mixture. The cellulose compound and distilled water are mixed for about five minutes. More water is added and the solution is mixed for about five more minutes. Solvent is added and mixed for about twenty more minutes. Variations of this method may be employed as illustrated by the foregoing examples with similar results obtained.

The following are examples of the most preferred methods of preparing aqueous nitrocellulose solutions:

SPECIFIC EXAMPLE 1

10 g of nitrocellulose and 20 g of distilled water were mixed for 5 minutes. 20 g of distilled water was added and the resulting solution mixed for 5 minutes. 40 g of ethylene glycol monobutyl acetate was poured into this solution and mixed for 20 minutes.

SPECIFIC EXAMPLE 2

10 g of nitrocellulose and 20 g of distilled water were mixed for 5 minutes. 20 g of distilled water was added and the resulting solution mixed for 5 minutes. 40 g of ethylene glycol monobutyl ether was poured into the mixture and mixed for 20 minutes.

SPECIFIC EXAMPLE 3

10 g of nitrocellulose and 20 g of distilled water were mixed for 5 minutes. 20 g of distilled water was added and the resulting solution mixed for 5 minutes. 0.5 g of CMC-7H-1% was added and this solution was mixed for 8 minutes. 40 g of ethylene glycol monobutyl ether was then poured into the solution and mixed for 20 minutes.

SPECIFIC EXAMPLE 4

10 g of nitrocellulose and 20 g of distilled water were mixed for 5 minutes. 20 g of distilled water was poured into the mixture and mixed for 5 minutes. 0.5 g of CMC-7H-1% was added and mixed in for 8 minutes. 40 g of ethylene glycol monobutyl acetate was poured into the mixture and mixed for 20 minutes.

SPECIFIC EXAMPLE 5

10 g of nitrocellulose and 40 g of distilled water were mixed for 5 minutes. 5 g of $NH_4OH$ (28%) and 40 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 6

10 g of nitrocellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 30 g of ethylene glycol monobutyl ether was poured into the mixture and mixed for 20 minutes.

The following are examples of the most preferred methods of preparing aqueous ethylcellulose solutions:

SPECIFIC EXAMPLE 7

10 g of ethylcellulose and 20 g of distilled water were mixed for 5 minutes. 20 g of distilled water was added and the resulting solution mixed for 5 minutes. 40 g of ethylene glycol monobutyl acetate was poured into this solution and mixed for 20 minutes.

SPECIFIC EXAMPLE 8

10 g of ethylcellulose and 20 g of distilled water were mixed for 5 minutes. 20 g of distilled water was added and the resulting solution mixed for 5 minutes. 40 g of ethylene glycol monobutyl ether was poured into the mixture and mixed for 20 minutes.

SPECIFIC EXAMPLE 9

10 g of ethylcellulose and 20 g of distilled water were mixed for 5 minutes. 20 g of distilled water was added and the resulting solution mixed for 5 minutes. 0.5 g of CMC-7H-1% was added and this solution was mixed for 8 minutes. 40 g of ethylene glycol monobutyl ether was then poured into the solution and mixed for 20 minutes.

SPECIFIC EXAMPLE 10

10 g of ethylcellulose and 20 g of distilled water were mixed for 5 minutes. 20 g of distilled water was poured into the mixture and mixed for 5 minutes. 0.5 g of CMC-7H-1% was added and mixed in for 8 minutes. 40 g of ethylene glycol monobutyl acetate was poured into the mixture and mixed for 20 minutes.

SPECIFIC EXAMPLE 11

10 g of ethylcellulose and 40 g of distilled water were mixed for 5 minutes. 5 g of $NH_4OH$ (28%) and 40 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 12

10 g of ethylcellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 30 g of ethylene glycol monobutyl ether was poured into the mixture and mixed for 20 minutes.

The following are examples of the most preferred methods of preparing aqueous cellulose acetate butyrate solutions:

SPECIFIC EXAMPLE 13

10 g of cellulose acetate butyrate and 20 g of distilled water were mixed for 5 minutes. 20 g of distilled water was added and the resulting solution mixed for 5 minutes. 40 g of ethylene glycol monobutyl acetate was poured into this solution and mixed for 20 minutes.

SPECIFIC EXAMPLE 14

10 g of cellulose acetate butyrate and 20 g of distilled water were mixed for 5 minutes. 20 g of distilled water was added and the resulting solution mixed for 5 minutes. 40 g of ethylene glycol monobutyl ether was poured into the mixture and mixed for 20 minutes.

SPECIFIC EXAMPLE 15

10 g of cellulose acetate butyrate and 20 g of distilled water were mixed for 5 minutes. 20 g of distilled water was added and the resulting solution mixed for 5 minutes. 0.5 g of CMC-7H-1% was added and this solution was mixed for 8 minutes. 40 g of ethylene glycol monobutyl ether was then poured into the solution and mixed for 20 minutes.

SPECIFIC EXAMPLE 16

10 g of cellulose acetate butyrate and 20 g of distilled water were mixed for 5 minutes. 20 g of distilled water was poured into the mixture and mixed for 5 minutes. 0.5 g of CMC-7H-1% was added and mixed in for 8 minutes. 40 g of ethylene glycol monobutyl acetate was poured into the mixture and mixed for 20 minutes.

SPECIFIC EXAMPLE 17

10 g of cellulose acetate butyrate and 40 g of distilled water were mixed for 5 minutes. 5 g of NH$_4$OH (28%) and 40 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 18

10 g of cellulose acetate butyrate and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether was poured into the mixture and mixed for 20 minutes.

The following are examples of the preferred method of preparing aqueous nitrocellulose solutions:

SPECIFIC EXAMPLE 19

10 g of nitrocellulose and 30 g of distilled water were mixed for 5 minutes. 5 g of NH$_4$OH (28%) and 45 g of distilled water were combined and poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 20

10 g of nitrocellulose and 30 g of distilled water were mixed for 5 minutes. 5 g of NH$_4$OH (28%) and 45 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 21

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl acetate was poured into the mixture and mixed for 30 minutes.

SPECIFIC EXAMPLE 22

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl ether was poured into the mixture and mixed for 20 minutes.

SPECIFIC EXAMPLE 23

10 g of nitrocellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 24

10 g of nitrocellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl ether was poured into the mixture and mixed for 20 minutes.

The following are examples of the preferred method of preparing aqueous ethylcellulose solutions:

SPECIFIC EXAMPLE 25

10 g of ethylcellulose and 30 g of distilled water were mixed for 5 minutes. 5 g of NH$_4$OH (28%) and 45 g of distilled water were combined and poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 26

10 g of ethylcellulose and 30 g of distilled water were mixed for 5 minutes. 5 g of NH$_4$OH (28%) and 45 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 27

10 g of ethylcellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl acetate was poured into the mixture and mixed for 30 minutes.

SPECIFIC EXAMPLE 28

10 g of ethylcellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl ether was poured into the mixture and mixed for 20 minutes.

SPECIFIC EXAMPLE 29

10 g of ethylcellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 30

10 g of ethylcellulose and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl ether was poured into the mixture and mixed for 20 minutes.

The following are examples of the preferred method of preparing aqueous cellulose acetate butyrate solutions:

SPECIFIC EXAMPLE 31

10 g of cellulose acetate butyrate and 30 g of distilled water were mixed for 5 minutes. 5 g of NH$_4$OH (28%) and 45 g of distilled water were combined and poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 32

10 g of cellulose acetate butyrate and 30 g of distilled water were mixed for 5 minutes. 5 g of NH$_4$OH (28%) and 45 g of distilled water were combined, poured into the mixture and mixed for 5 minutes. 0.5 g of CMC-7H-1% was added and mixed for 8 minutes. 40 g of ethylene glycol monobutyl ether was poured into the mixture and mixed for 20 minutes.

SPECIFIC EXAMPLE 33

10 g of cellulose acetate butyrate and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl acetate was poured into the mixture and mixed for 30 minutes.

SPECIFIC EXAMPLE 34

10 g of cellulose acetate butyrate and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 46 g of ethylene glycol monobutyl ether was poured into the mixture and mixed for 20 minutes.

SPECIFIC EXAMPLE 35

10 g of cellulose acetate butyrate and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl acetate was poured into the mixture and mixed for 20 minutes.

SPECIFIC EXAMPLE 36

10 g of cellulose acetate butyrate and 25 g of distilled water were mixed for 5 minutes. 25 g of distilled water was poured into the mixture and mixed for 5 minutes. 0.5 g of CMC-7H-1% was added and mixed for 8 minutes. 40 g of ethylene glycol monobutyl ether was poured into the mixture and mixed for 20 minutes.

The following are additional examples of the method of preparing aqueous nitrocellulose solutions:

SPECIFIC EXAMPLE 37

10 g of nitrocellulose and 30 g of distilled water were mixed for 5 minutes. 5 g of NH$_4$OH (28%) and 45 g of distilled water were combined, poured into the mixture and mixed for 5 minutes. 0.5 g of CMC-7H 1% was added and mixed for 8 minutes. 2 g of Zn(NH$_3$)3×(CO$_3$)×(Zinc Ammonia Carbonate Complex) and 8 g of distilled water were mixed in for 10 minutes. 35 g of ethylene glycol monobutyl acetate was poured into the mixture and mixed for 40 minutes.

SPECIFIC EXAMPLE 38

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 20 g of ethylene glycol monobutyl ether and 26 g of isopropyl acetate were combined, poured into the mixture and mixed for 20 minutes.

SPECIFIC EXAMPLE 39

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of diethylene glycol monoethyl ether were combined, poured into the mixture and mixed for 20 minutes.

SPECIFIC EXAMPLE 40

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of ethylene glycol monobutyl acetate were combined, poured into the mixture and mixed for 25 minutes.

SPECIFIC EXAMPLE 41

10 g of nitrocellulose and 16.44 g of distilled water were mixed for 5 minutes. 5 g of NH$_4$OH (28%) and 24.52 g of distilled water were combined, poured into the mixture and mixed for 5 minutes. 0.5 g of CMC-7H-1% was added and mixed for 8 minutes. 23 g of ethylene glycol monobutyl ether and 23 g of ethylene glycol monobutyl acetate were combined, poured into the mixture and mixed for 25 minutes.

SPECIFIC EXAMPLE 42

10 g of nitrocellulose and 16.44 g of distilled water were mixed for 5 minutes. 5 g of $NH_4OH$ (28%) and 24.52 g of distilled water were combined, poured into the mixture and mixed for 5 minutes. 0.5 g of CMC-7H-1% was added and mixed for 8 minutes. 30 g of ethylene glycol monobutyl ether and 16 g of ethylene glycol monobutyl acetate were combined, poured into the mixture and mixed for 25 minutes.

SPECIFIC EXAMPLE 43

10 g of nitrocellulose and 20 g of distilled water were mixed for 5 minutes. 20 g of distilled water was poured into the mixture and mixed for 5 minutes. 0.5 g of CMC-7H-1% was added and mixed for 8 minutes. 40 g of N-methyl-2-pyrrolidone was poured into the mixture and mixed for 20 minutes.

SPECIFIC EXAMPLE 44

10 g of nitrocellulose and 20 g of distilled water were mixed for 5 minutes. 20 g of distilled water was poured into the mixture and mixed for 5 minutes. 0.5 g of CMC-7H-1% was added and mixed for 8 minutes. 1 g of CO 630 was added. 40 g of ethylene glycol monobutyl acetate was poured into the mixture and mixed for 20 minutes.

II. Cellulose Based Coatings

Nitrocellulose-based coatings according to the present invention are obtained by mixing a proportional amount of acrylic-based polymers and aqueous nitrocellulose solution. It will be appreciated that alternatively, a proportional amount of acrylic-based polymers may be mixed with an aqueous ethylcellulose solution or aqueous cellulose acetate butyrate solution in a similar fashion to form ethylcellulose-based coatings and cellulose acetate butyrate-based coatings. Examples of polymers used in the present invention include but are not limited to A 1054, A 5050, R960 and BT 44, available from Zeneca Resins of Wilmington, Del., KRS 2411 and KPS 5545, available from Kane International Corp. of Larchmont, N.Y., ZINPOL 25 g, available from Zinchem, Inc. of Somerset, N.J., and CARBOSET 525 and CARBOSET 526, available from B. F. Goodrich Co. of Akron, Ohio. The preferred acrylic-based polymers are A621, A 622, A623, A630, A633, A645, A 655 and A 1054, available from Zeneca Resins and JONCRYL 77 and JONCRYL 89, available from S C Johnson of Racine, Wis. The invention can also include surfactants such as El 620, available from Rhone Poulenc, FC129 FLUORAD, available from 3M, SURFYNOL DF-75, SURFYNOL S-104E and SURFYNOL S-104PG, available from Air Products, Inc., L 7001, and L7602, available from Union Carbide Corp., and A-196 and OT75, available from American Cyanamid, and SPAN 80, available from ICI Specialties of Wilmington, Del., and others known in the art. Specific silanes such as Z 6040, 25-additive and Z-6020, available from Dow Corning Corp. of Midland, Mich. and A 1100, available from Union Carbide Corp. as well as those known in the art may also be employed. The invention can also include titanates such as TYZOR LA and TYZOR LE, available from E. I. dupont deNemours & Co., Inc. of Wilmington, Del. (Silanes and titanates are hydrolyzed 24 hours prior to usage to prevent concentrated areas in solution.) Colloidal silicas such as NALCO 2326, NALCO 1115 and NALCO 1140, available from Nalco Chemical Co. of Chicago, Ill., and dispersants such as CT 136, available from Air Products, Inc. and L 7602, available from Union Carbide Corp., may also be employed. Defoamers such as S-104E and S-104 PG from Air Products (also used as a wetting agent) may also be employed. Germicides such as Dowicide, parabens, ammonium hydroxide and others known in the art may also be added. A preferred germicide is SUTTOCIDE A, sold by Sutton Laboratory, Inc., a GAF Company (aka ISP Manufacturing). Thickeners such as SCT 270 and SCT 275, available from Union Carbide Corp., CMC-7H, available from Aqualon Co., and others known in the art may be added. A preferred thickener is KELTROL T, sold by Kelco Company, a division of Merck. The amount of germicides and thickeners added to the solution is based on the percentage level of solids in the solution. The amount of thickener used is in the range of about 0.4 to about 1.5% by weight and the amount of germicide used is also in the range of about 0.4 to about 1.5% weight. Solvents may be added to retard film formation and to allow better flow and freeze-thaw properties of the coating. Preferred solvents include ethanol (100%) or propylene glycol in the range of from about 8% by weight to about 10% by weight. Ultraviolet (UV) absorbers may also be employed to retard degradation of the coatings caused by UV radiation. Examples of suitable UV absorbers include SPECTRASORB UV 5411 and UV 531 sold by American Cyanamid, and UVINOL N-35, Etocrylene, sold by BASF. The amount of UV absorber used is in the range of about 0.2 to about 2% by weight.

The following methods were employed to formulate the nitrocellulose-based coatings. Generally, the material was placed in a 1000 ml beaker and a standard laboratory mixer was employed using a standard propeller, at room temperature. The mixer speed was set at 8.5 or at a speed great enough to form a vortex in the mixture. The solution was poured in a steady stream. A further step of decanting may be employed if necessary. Further illustrations of the basic method are depicted in the following examples.

SPECIFIC EXAMPLE 45

20 g of CARBOSET 525 (15%) and 10 g of distilled water were mixed together in a vessel and added to 2.9 g (based on solid content) of aqueous nitrocellulose solution (prepared as described above) and mixed for 10 minutes. 20 g of ZINPOL 259 was added and mixed for 10 minutes with the mixer speed increased to 8 setting. 10 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of distilled water and 10 g of ammonia hydroxide (10%) were poured together, mixed in a vessel, added to the above mixture and mixed for 10 minutes. 15 g of BT 44 was added and mixed for 10 minutes. 2.52 g of DF-75 (10%) at 0.5% level of solids was added and mixed for 15 minutes. 5.04 g of S-104E (1%) at 0.05% level of solids was added and mixed for 30 minutes. 5.04 g of FC-129 (0.01%) at 0.05% level of solids was added and mixed for 15 minutes. 2.52 g of Z 6040 (10%) at 0.5% level of solids was added and mixed for 15 minutes. 5.04 g of TYZOR LA (10%) at 1% level of solids was added and mixed for 15 minutes. 2.52 g of Z 6020 (10%) at 0.5% level of solids was added and mixed for 15 minutes. 2.52 g of A 1100 (10%) at 0.5% level of solids was added and mixed for 15 minutes. 5 g of ethylene glycol at 10% of solids was added and mixed for 15 minutes. 2.52 g of L 7001 (1%) at 0.5% level of solids was added and mixed for 15 minutes. 0.3 g of N 2326 (10%) at 0.5% level of solids was added and mixed for 15 minutes. 0.3 g of N 1115 (10%) at 0.5% level of solids was added and mixed for 15 minutes. 2.52 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 46

16 g of C 525 and 10 g of distilled water were combined. 2.9 g solid weight (based on solid content) of aqueous nitrocellulose solution (prepared as described above) was added. 10 g of BT 44 was added and mixed for 10 minutes. 25 g of A 622 was added and mixed for 10 minutes. 15 g of A 655 was added and mixed for 10 minutes. 15 g of Z 259 was added and mixed for 10 minutes. 5 g of KRS 2411 was added and mixed for 10 minutes. 20 g of A 1054 was added and mixed for 10 minutes. 10 g of distilled water was added and mixed for 10 minutes. 10 g of NH$_4$OH (10%) was added and mixed for 10 minutes. 2.2 g of DF 75 (10%) at 0.5% level of solids was added and mixed for 15 minutes. 4.4 g of S 104E (1%) at 0.05% level of solids was added and mixed for 30 minutes. 4.4 g of FC 129 (0.01%) at 0.05% level of solids was added and mixed for 30 minutes. 2.2 g of Z 6040 (10%) at 0.5% level of solids was added and mixed for 15 minutes. 4.4 g of TYZOR LA(10%) at 1% level of solids was added and mixed for 15 minutes. 2.2 g of Z 6020 (10%) at 0.5% level of solids was added and mixed for 15 minutes. 2.2 g of A 1100 (10%) at 0.5% level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.2 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 47

16 g of C 525 (15%) and 10 g of distilled water were combined. 2.9 g (based on solid content) of aqueous nitrocellulose solution (prepared as described above) was added. 20 g of Z 259 was added and mixed for 10 minutes. 10 g of KRS 2411 was added and mixed for 10 minutes. 25 g of A 622 and 15 g of A 655 was added and mixed for 10 minutes. 20 g of A 1054 was added and mixed for 10 minutes. 10 g of distilled water was added and mixed for 10 minutes. 10 g of NH$_4$OH (10%) was added and mixed for 10 minutes. 15 g of BT 44 was added and mixed for 10 minutes. 15 g of A 5050 was added and mixed for 10 minutes. 2.8 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of TYZOR LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at 0.5% level of solids was added and mixed for 15 minutes. 5 g of ethylene glycol 10% of solids was added and mixed for 15 minutes. 1 g of 25-additive (3%) at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 48

15 g of BT 44 and 25 g of A 622 were mixed together for 10 minutes. 10 g of A 1054 was added and mixed for 10 minutes. 15 g of A 655 was added and mixed for 10 minutes. 10 g of KRS 2411 was added and mixed for 10 minutes. 15 g of C 525 and 10 g of distilled water were combined, added to the above mixture and mixed for 10 minutes. 20 g of Z 259 was added and mixed for 10 minutes. 10 g of distilled water was added and mixed for 10 minutes. 10 g of NH$_4$OH (10%) was added and mixed for 10 minutes. 2.9 g (based on solid content) of aqueous nitrocellulose solution (prepared as described above) was added and mixed for 10 minutes. 4.72 g of S 104E (1%) at 0.05% level of solids was added and mixed for 30 minutes. 2.56 g of DF 75 (10%) at 0.5% level of solids was added and mixed for 15 minutes. 4.72 g of FC 129 (0.01%) at 0.5% level of solids was added and mixed for 30 minutes. 2.36 g of Z 6040 (10%) at 0.5% level of solids was added and mixed for 15 minutes. 4.72 g of TYZOR LA (10%) at 1% level of solids was added and mixed for 15 minutes. 2.36 g of Z 6020 (10%) at 0.5% level of solids was added and mixed for 15 minutes. 2.36 g of A 1100 (10%) at 0.5% level of solids was added and mixed for 15 minutes. 2.36 g of L 7001 (1%) at 0.5% level of solids was added and mixed for 15 minutes. 4.6 g of ethylene glycol at 10% of solids was added and mixed for 15 minutes. 1.02 g of 25-additive at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.36 g of A 196 (1%) at 0.5% level of solids was added and mixed for 15 minutes. 0.47 g of CMC-7H-1% at 0.0625% level of solids was added and mixed for 30 minutes.

SPECIFIC EXAMPLE 49

2.9 g (based on solid content) of aqueous nitrocellulose solution (prepared as described above) was added to the vessel. 16 g of C 525 and 10 g of distilled water were combined, added to the vessel and mixed for 10 minutes. 25 g of A 622 was added and mixed for 10 minutes. 15 g of A 655 was added and mixed for 10 minutes. 15 g of Z 259 was added and mixed for 10 minutes. 15 g of BT 44 was added and mixed for 10 minutes. 20 g of A 1054 was added and mixed for 10 minutes. 10 g of NH$_4$OH (10%) was added and mixed for 10 minutes. 10 g of distilled water was added and mixed for 10 minutes. 2.25 g of DF 75 (10%) at 0.5% level of solids was added and mixed for 15 minutes. 4.5 g of S 104E (1%) at 0.05% level of solids was added and mixed for 30 minutes. 4.5 g of FC 129 (0.01%) at 0.05% level of solids was added and mixed for 30 minutes. 2.25 g of Z 6040 (10%) at 0.5% level of solids was added and mixed for 15 minutes. 4.5 g of TYZOR LA (10%) at 1% level of solids was added and mixed for 15 minutes. 2.25 g of Z 6020 (10%) at 0.5% level of solids was added and mixed for 15 minutes. 2.25 g of A 1100 (10%) at 0.5% level of solids was added and mixed for 15 minutes. 2.25 g of L 7001 (1%) at 0.5% level of solids was added and mixed for 15 minutes. 5 g of ethylene glycol at 10% of solids was added and mixed for 15 minutes. 1 g of 25-additive at 0.05% of solids was added and mixed for 15 minutes. 0.5 g of N 2325 (10%) at 0.5% level of solids was added and mixed for 15 minutes. 0.5 g of N 1115 (10%) at 0.5% level of solids was added and mixed for 15 minutes. 2.25 g of A 190 (1%) at 0.5% level of solids was added and mixed for 15 minutes. 0.5 g of CMC-7H-1% at 0.0625% level of solids was added and mixed for 30 minutes.

SPECIFIC EXAMPLE 50

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g (based on solid content) of aqueous nitrocellulose solution (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 2.71 g of DF 75 (10%) at 0.5% level of solids was added and mixed for 15 minutes. 5.42 g of S 104E (1%) at 0.05% level of solids was added and mixed for 30 minutes. 5.42 g of FC 129 (0.01%) at 0.05% level of solids was added and mixed for 30 minutes. 2.71 g of Z 6040 (10%) at 0.5% level of solids was added and mixed for 15 minutes. 5.42 g of TYZOR LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L7001 (1%) at 0.5% level of solids was added and mixed for 15 minutes. 4.86 g of ethylene glycol at 8% of solids was added and mixed for 15 minutes. 1.25 g of 25-additive at 0.05% level of solids was added and mixed for 15 minutes. 0.54 g of N 2325 (10%) at 0.5% volume of solids was added and mixed for 15 minutes. 0.54 g of N 1115 (10%) at 0.5% volume of solids was added and mixed for 15 minutes. 2.71 g of A 196 (1%) at 0.5% level of solids was added and mixed for 15 minutes. 0.54 g of CMC-7H-1% at 0.0625% level of solids was added and mixed for 30 minutes.

SPECIFIC EXAMPLE 51

20 g of A 1054 and 15 g of BT 44 were combined and mixed for 10 minutes. 10 g of distilled water was added and mixed for 10 minutes. 15 g of A 655 was added and mixed for 10 minutes. 25 g of A 622 was added and mixed for 10 minutes. 2.9 g (based on solid content) of aqueous nitrocellulose solution (prepared as described above) was added and mixed for 10 minutes. 10 g of distilled water was added and mixed for 10 minutes. 10 g of $NH_4OH$ (10%) was added and mixed for 10 minutes. 20 g of Z 259 was added and mixed for 10 minutes. 10 g of KRS 2411 was added and mixed for 10 minutes. 10 g of KRS 5545 was added and mixed for 10 minutes. 20 g of C 525 was added and mixed for 10 minutes. 2.71 g of DF 75 (10%) at 0.5% level of solids was added and mixed for 15 minutes. 5.42 g of S 104E (1%) at 0.05% level of solids was added and mixed for 30 minutes. 5.42 g of FC 129 (0.01%) at 0.05% level of solids was added and mixed for 30 minutes. 2.71 g of Z 6040 (10%) at 0.5% level of solids was added and mixed for 15 minutes. 5.42 g of TYZOR LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L 7001 (1%) at 0.5% level of solids was added and mixed for 15 minutes. 4.86 g of ethylene glycol at 8% of solids was added and mixed for 15 minutes. 1.25 g of 25-additive at 0.05% of solids was added and mixed for 15 minutes. 0.54 g of N 2326 (10%) at 0.5% level of solids was added and mixed for 15 minutes. 0.54 g of N 1115 (10%) at 0.5% level of solids was added and mixed for 15 minutes. 2.71 g of A 196 (1%) at 0.5% level of solids was added and mixed for 10 minutes. 0.54 g of CMC-7H-1% at 0.0625% level of solids was added and mixed for 30 minutes.

SPECIFIC EXAMPLE 52

2.9 g (based on solid content) of aqueous nitrocellulose solution (prepared as described above) was added to the vessel. 16 g of C 525 and 10 g of distilled water were combined, added to the vessel and mixed for 10 minutes. 10 g of BT 44 was added and mixed for 10 minutes. 25 g of A 622 was added and mixed for 10 minutes. 15 g of A 655 was added and mixed for 10 minutes. 15 g of Z 269 was added and mixed for 10 minutes. 20 g of A 1054 was added and mixed for 10 minutes. 10 g of distilled water was added and mixed for 10 minutes. 10 g of $NH_4OH$ (10%) was added and mixed for 10 minutes. 2.2 g of DF 75 (10%) at 0.5% level of solids was added and mixed for 15 minutes. 4.4 g of FC 129 (0.01%) at. 0.05% level of solids was added and mixed for 30 minutes. 2.2 g of Z 6040 (10%) at 0.5% level of solids was added and mixed for 15 minutes. 4.4 g of TYZOR LA (10%) at 1% level of solids was added and mixed for 15 minutes. 2.2 g of Z 6020 (10%) at 0.5% level of solids was added and mixed for 15 minutes. 2.2 g of A 1100 (10%) at 0.5% level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 4.4 g of S 104E (1%) at 0.05% level of solids was added and mixed for 30 minutes.

SPECIFIC EXAMPLE 53

2.9 g (based on solid content) of aqueous nitrocellulose solution (prepared as described above) and 15 g of BT 44 were combined and mixed for 10 minutes. 10 g of distilled water was added and mixed for 10 minutes. 20 g of A 1054 was added and mixed for 10 minutes. 15 g of A 655 was added and mixed for 10 minutes. 10 g of KRS 2411 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 20 g of Z 259 was added and mixed for 10 minutes. 25 g of A 622 was added and mixed for 10 minutes. 2.8 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of TYZOR LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at 0.5% level of solids was added and mixed for 15 minutes. 5 g of ethylene glycol at 10% of solids was added and mixed for 15 minutes. 1 g of 25-additive (3%) at 0.05% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 54

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g solid weight (based on solid content) aqueous nitrocellulose solution (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 2.71 g of DF 75 (10%) at 0.5% level of solids was added and mixed for 15 minutes. 5.42 g of S 104E (1%) at 0.05% level of solids was added and mixed for 30 minutes. 5.42 g of FC 129 (0.01%) at 0.05% level of solids was added and mixed for 30 minutes. 2.71 g of Z 6040 (10%) at 0.5% level of solids was added and mixed for 15 minutes. 5.42 g of TYZOR LA (10%) at 1% level of solids was added and mixed for 15 minutes. 2.71 g of Z 6020 (10%) at 0.5% level of solids was added and mixed for 15 minutes. 2.71 g of A 1100 (10%) at 0.5% level of solids was added and mixed for 15 minutes. 2.71 g of L 7001 (1%) at 0.5% level of solids was added and mixed for 15 minutes. 4.86 g of ethylene glycol at 8% of solids was added and mixed for 15 minutes. 1.25 g of 25-additive at 0.05% of solids was added and mixed for 15 minutes. 0.54 g of N 2326 (10%) at 0.5% level of solids was added and mixed for 15 minutes. 0.54 g of N 1115 (10%) at 0.5% level of solids was added and mixed for 15 minutes. 2.71 g of A 196 (1%) at 0.5% level of solids was added and mixed for 15 minutes. 0.54 g of CMC-7H (1%) at 0.0625% level of solids was added and mixed for 30 minutes.

SPECIFIC EXAMPLE 55

20 g of A 1054 was added to the vessel. 20 g of C 525 and 10 g of distilled water were combined, added to the vessel and mixed for 10 minutes. 15 g of A 655 was added and mixed for 10 minutes. 15 g of BT 44 was added and mixed for 10 minutes. 2.9 g (based on solid content) of aqueous nitrocellulose solution (prepared as described above) was added and mixed for 10 minutes. 25 g of A 622 was added and mixed for 10 minutes. 10 g of KRS 2411 was added and mixed for 10 minutes. 20 g of Z 259 was added and mixed for 10 minutes. 10 g of KRS 5545 was added and mixed for 10 minutes. 10 g of distilled water was added and mixed for 10 minutes. 10 g of $NH_4OH$ (10%) was added and mixed for 10 minutes. 2.6 g of DF 75 (10%) at 0.5% level of solids was added and mixed for 15 minutes. 5.6 g of S 104E (1%) at 0.05% level of solids was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of TYZOR LA (10%) at 1% level of solids was added and mixed for 15 minutes. 2.8 g of Z 6020 (10%) at 0.5% level of solids was added and mixed for 15 minutes. 2.8 g of 1100 (10%) at 0.5% level of solids was added and mixed for 15 minutes. 2.8 g of L 7001 (1%) at 0.5% level of solids was added and mixed for 15 minutes. 5 g of ethylene glycol at 10% of solids was added and mixed for 15 minutes. 1 g of 25-additive (3%) at 0.05% of solids was added and mixed for 15 minutes. 0.5 g of N 2326 (10%) at −0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 56

2.9 g (based on solid content) of aqueous nitrocellulose solution (prepared as described above) was added to the vessel. 16 g of C 525 (15%) and 10 g of distilled water were combined, added to the vessel and mixed for 10 minutes. 20 g of Z 259 was added and mixed for 10 minutes. 25 g of A 622 was added and mixed for 10 minutes. 15 g of A 655 was added and mixed for 10 minutes. 15 g of BT 44 was added and mixed for 10 minutes. 20 g of A 1054 was added and mixed for 10 minutes. 10 g of KRS 2411 was added and mixed for 10 minutes. 10 g of $NH_4OH$ (10%) was added and mixed for 10 minutes. 2.8 g of DF 75 (10%) at 0.5% level of solids was added and mixed for 15 minutes. 5.6 g of S 104E (1%) at 0.05% was added and mixed for 30 minutes. 5.6 g of FC 129 (0.01%) at 0.05% level of solids was added and mixed for 30 minutes. 2.8 g of Z 6040 (10%) at 0.5% level of solids was added and mixed for 15 minutes. 5.6 g of TYZOR LA (10%) at 1% level of solids was added and mixed for 15 minutes. 2.8 g of Z 6020 (10%) at 0.5% level of solids was added and mixed for 15 minutes. 2.8 g of A 1100 (10%) at 0.5% level of solids was added and mixed for 15 minutes. 2.8 g of L 7001 (1%) at 0.5% level of solids was added and mixed for 15 minutes. 5 g of ethylene glycol at 10% of solids was added and mixed for 15 minutes. 0.5 g of N 2326 (10%) at 0.5% level of solids was added and mixed for 15 minutes. 0.5 g of N 1115 (10%) at 0.5% level of solids was added and mixed for 15 minutes. 2.8 g of A 196 (1%) at 0.5% level of solids was added and mixed for 15 minutes. 0.5 g of CMC-7H (1%) at 0.0625% level of solids was added and mixed for 30 minutes.

SPECIFIC EXAMPLE 57

2.9 g (based on solid content) of aqueous nitrocellulose solution (prepared as described above) was added to the vessel. 20 g of C 525 (15%) and 10 g of distilled water were combined, added to the vessel and mixed for 10 minutes. 20 g of Z 259 was added and mixed for 10 minutes. 25 g of A 622 was added and mixed for 10 minutes. 15 g of A 655 was added and mixed for 10 minutes. 15 g of BT 44 was added and mixed for 10 minutes. 20 g of A 1054 was added and mixed for 10 minutes. 10 g of KRS 2411 was added and mixed for 10 minutes. 10 g of $NH_4OH$ (10%) was added and mixed for 10 minutes. 3 g of DF 75 (10%) at 0.6% level of solids was added and mixed for 15 minutes. 5.02 g of S 104E (1%) at 0.05% level of solids was added and mixed for 30 minutes. 5.02 g of FC 129 (0.01%) at 0.05% level of solids was added and mixed for 30 minutes. 5.01 g of Z 6040 (10%) at 1.02% level of solids was added and mixed for 15 minutes. 10 g of TYZOR LA (10%) at 2% level of solids was added and mixed for 15 minutes. 5.01 g of Z 6020 (10%) at 1.02% level of solids was added and mixed for 15 minutes. 5.01 g of A 1100 (10%) at 1.02% level of solids was added and mixed for 15 minutes. 2.5 g of L 7001 (1%) at 0.5% level of solids was added and mixed for 15 minutes. 5 g of ethylene glycol at 10% of solids was added and mixed for 15 minutes. 0.25 g of N 2326 (10%) at 0.5% level of solids was added and mixed for 15 minutes. 0.25 g of N 1115 (10%) at 0.5% level of solids was added and mixed for 15 minutes. 2.5 g of A 196 (1%) at 0.5% level of solids was added and mixed for 30 minutes.

SPECIFIC EXAMPLE 58

2.9 g (based on solid content) of aqueous nitrocellulose solution (prepared as described above) was added to the vessel. 20 g of C 525 (15%) and 10 g of distilled water were combined, added to the vessel and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 10 g of $NH_4OH$ (10%) was added and mixed for 10 minutes. 3 g of DF 75 (10%) at 0.6% level of solids was added and mixed for 15 minutes. 5.6 g of FC 129 (0.01%) at 0.06% level of solids was added and mixed for 30 minutes. 5.01 g of S 104E (1%) at 0.05% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 0.5 g of CMC-7H (1%) at 0.0625% level of solids was added and mixed for 30 minutes.

SPECIFIC EXAMPLE 59

2.9 g (based on solid content) of aqueous nitrocellulose solution (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of $NH_4OH$ (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 30 minutes.

SPECIFIC EXAMPLE 60

2.9 g (based on solid content) of aqueous nitrocellulose solution (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of $NH_4OH$ (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 3.01 g of SCT 270 1% of solids was added and mixed for 30 minutes.

SPECIFIC EXAMPLE 61

2.9 g (based on solid content) of aqueous nitrocellulose solution (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of $NH_4OH$ (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A196 (1%) at 0.06% level of solids was added and mixed for 15 minutes. 2.20 g of SCT 270 0.75% of solids was added and mixed for 30 minutes.

SPECIFIC EXAMPLE 62

2.9 g (based on solid content) of aqueous nitrocellulose solution (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 2.04 g of SCT 270 at 0.75% level of solids was added and mixed for 30 minutes.

SPECIFIC EXAMPLE 63

2.9 g (based on solid content) of aqueous nitrocellulose solution (prepared as described above) was added to the vessel. 20 g of C 525 (15%) and 10 g of distilled water were combined, added to the vessel and mixed for 10 minutes. 10 g of C 526 (10%) was added and mixed for 10 minutes. 20 g of Z 259 was added and mixed for 10 minutes. 12 g of KRS 2411 was added and mixed for 10 minutes. 25 g of A 622 was added and mixed for 10 minutes. 15 g of A 655 was added and mixed for 10 minutes. 20 g of A 1054 was added and mixed for 10 minutes. 10 g of BT 44 was added and mixed for 10 minutes. 5 g of NH$_4$OH (10%) was added and mixed for 10 minutes. 3.05 g of DF 75 (10%) at 0.6% level of solids was added and mixed for 15 minutes. 5.01 g of S 104E (1%) at 0.05% level of solids was added and mixed for 30 minutes. 6 g of FC 129 (0.01%) at 0.06% level of solids was added and mixed for 30 minutes. 4 g of Z 6040 (10%) at 0.8% level of solids was added and mixed for 15 minutes. 10 g of TYZOR LA (10%) at 1% level of solids was added and mixed for 15 minutes. 4 g of Z 6020 (10%) at 0.8% level of solids was added and mixed for 15 minutes. 4 g of A 1100 (10%) at 0.8% level of solids was added and mixed for 15 minutes. 3 g of L 7001 (1%) at 0.06% level of solids was added and mixed for 15 minutes. 5 g of ethylene glycol at 10% of solids was added and mixed for 15 minutes. 0.5 g of N 2326 (10%) at 1% level of solids was added and mixed for 15 minutes. 0.5 g of N 1115 (10%) at 1% level of solids was added and mixed for 15 minutes. 3 g of A 196 (1%) at 0.06% level of solids was added and mixed for 15 minutes. 2.73 g of SCT 270 at 1% level of solids was added and mixed for 30 minutes.

III. Modified Polymers in Cellulose Based Coatings

In a preferred method, polymers were modified with an aqueous nitrocellulose solution or aqueous ethylcellulose solution or aqueous cellulose acetate butyrate solution in a range between 0.01 g and 1.0 g of aqueous cellulose solution per gram polymer. This is determined by the viscosity of the resulting mix, which is allowed to react from three to twenty days and is determined by clarity of film on glass prior to formulating the coatings. The modification optimizes the amount of cellulose in solution producing an increase in the percent of cellulose in the coating. The modified method produces coatings with increased clarity, viscosity, flexibility and hardness. The same basic method for formulating the coatings, as described above, is employed with the exception of using the modified polymers.

The following method was employed to formulate the modified polymers. Generally, polymer and aqueous nitrocellulose are mixed in a 1000 ml beaker. A water bath with a temperature of from about 70° to about 95° C. may be employed to accelerate the reaction. The solution is then placed in a container and sits for a few days to several weeks to allow for reaction. A further step of decanting may be employed if necessary. The ratio of aqueous nitrocellulose solution to polymer varies for particular polymers.

The most preferred ratio of aqueous nitrocellulose solution to polymer is as follows:
0.066 g aqueous nitrocellulose solution per 1 g A622
0.04 g aqueous nitrocellulose solution per 1 g A655
0.039 g aqueous nitrocellulose solution per 1 g A1054
0.0213 g aqueous nitrocellulose solution per 1 g KRS2411
0.022 g aqueous nitrocellulose solution per 1 g Z259
0.05748 g aqueous nitrocellulose solution per 1 g C525
0.0678 g aqueous nitrocellulose solution per 1 g BT44
0.0201 g aqueous nitrocellulose solution per 1 g R960
0.0615 g of aqueous nitrocellulose solution per 1 g A621
0.06 g of aqueous nitrocellulose solution per 1 g A630

As described above, the general method for formulating nitrocellulose based coatings is employed using modified polymers. Illustrations of this basic method using modified polymers in the most preferred embodiment of the present invention is depicted in the following examples.

The following are examples of the methods of making the most preferred modified coatings:

SPECIFIC EXAMPLE 64

60 g of modified A630 and 60 g of modified A655 were mixed for 10 minutes. 40 g of modified A622 was added and mixed for 10 minutes. 20 g of modified A1054 was added and mixed for 10 minutes. 0.44 g of FC129 5% at 0.015% of solids at 50% active was added and mixed for 25 minutes. 2.04 g of L7602 5% at 0.14% of solids was added and mixed for 20 minutes. 0.364 g of Z6040 100% at 0.5% of solids was added and mixed for 20 minutes. 1.45 g of TYZOR La 100% at 1% of solids at 50% active was added and mixed for 20 minutes. 0.73 g of SUTTOCIDE A 100% at 0.5% of solids at 50% active was added and mixed for 20 minutes. 9.09 g of NALCO 1140 40% at 5% of solids was added and mixed for 20 minutes. 3.42 g of A196 100% at 0.4% of solids at 85% active was added and mixed for 20 minutes. 0.29 g of OT75 100% at 0.3% of solids at 75% active was added and mixed for 20 minutes. 0.15 g of SPAN80 100% at 0.2% of solids was added and mixed for 20 minutes. 63.95 g of A630, unmodified, at 31.5% of total volume was added and mixed for 15 minutes. 19.61 g of A633, unmodified, at 9.66% of total volume was added and mixed for 15 minutes. 28.28 g of A645, unmodified, at 20% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids, as required.

SPECIFIC EXAMPLE 65

60 g of modified A630 and 60 g of modified A655 were mixed for 10 minutes. 40 g of modified A622 was added and mixed for 10 minutes. 20 g of modified A1054 was added and mixed for 10 minutes. 0.44 g of FC129 5% at 0.015% of solids at 50% active was added and mixed for 25 minutes. 2.04 g of L7602 5% at 0.14% of solids was added and mixed for 20 minutes. 0.364 g of Z6040 100% at 0.5% of solids was added and mixed for 20 minutes. 1.45 g of TYZOR La 100% at 1% of solids at 50% active was added and mixed for 20 minutes. 0.73 g of SUTTOCIDE A 100% at 0.5% of solids at 50% active was added and mixed for 20 minutes. 9.09 g of NALCO 1140 40% at 5% of solids was added and mixed for 20 minutes. 3.42 g of A196 100% at 0.4% of solids at 85% active was added and mixed for 20 minutes. 0.29 g of OT75 100% at 0.3% of solids at 75% active was added and mixed for 20 minutes. 0.15 g of SPAN80 100% at 0.2% of solids was added and mixed for 20 minutes. 63.95 g of A630, unmodified, at 31.5% of total volume was added and mixed for 15 minutes. 19.61 g of A633, unmodified, at 9.66% of total volume was added and mixed for 15 minutes. 28.28 g of A623, unmodified, at 20% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

SPECIFIC EXAMPLE 66

360 g of modified A622 and 216 g of modified A655 was mixed for 20 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 120 g of modified A1054 was added and mixed for 25 minutes. 57.3 g of ethanol 200% proof and 14.32 g of distilled water were added and mixed for 25 minutes. 2.18 g of SUTTOCIDE A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

SPECIFIC EXAMPLE 67

180 g of modified A622 and 108 g of modified A655 were mixed together for 10 minutes. 60 g of modified A1054 was added and mixed for 10 minutes. 4.54 g of L7602 4% at 0.15% of solids was added and mixed for 15 minutes. 3.63 g of SILWET 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 37.75% of solids. U.V. absorber 1% level of 10% solution is 6.795 g of SPECTRASORB UV 5411.

SPECIFIC EXAMPLE 68

180 g of modified A622 and 108 g of modified A655 were mixed together for 10 minutes. 60 g of modified A1054 was added and mixed for 10 minutes. 60 g of modified R960 was added and mixed for 10 minutes. 4.54 g of L7602 4% at 0.15% of solids was added and mixed for 15 minutes. 3.63 g of SILWET 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 37.75% of solids. U.V. absorber 1% level of 10% solution is 6.795 g of SPECTRASORB UV 5411.

SPECIFIC EXAMPLE 69

360 g of modified A622 and 216 g of modified A655 was mixed for 20 minutes. 120 g of modified A1054 was added and mixed for 20 minutes. 4.76 g of L7602 10% at 0.18% level of solids was added and mixed for 25 minutes. 7.93 g of S77 1% at 0.03% level of solids was added and mixed for 30 minutes. 0.88 g of N1115 100% at 0.05% level of solids at 15% active was added and mixed for 25 minutes. 2.12 g of Z6040 100% at 0.8% level of solids was added and mixed for 25 minutes. 8.46 g of TYZOR LA 100% at 1.6% level of solids at 50% active was added and mixed for 25 minutes. 21.16 g of propylene glycol 100% at 0.8% level of solids was added and mixed for 25 minutes. 2.64 g of SUTTOCIDE A 100% at 0.5% level of solids at 50% active was added and mixed for 25 minutes. The amount of solvent, defoamer, germicide and thickener was based on 38% of solids.

The following are examples of methods of making the preferred modified coatings:

SPECIFIC EXAMPLE 70

50.2 g of modified A621 and 50.2 g of modified A655 were mixed for 10 minutes. 36 g of modified A622 was added and mixed for 10 minutes. 30 g of modified A1054 was added and mixed for 10 minutes. 2.05 g of FC129 1% at 0.015% of solids at 50% active was added and mixed for 25 minutes. 0.96 g of L7602 10% at 0.14% of solids was added and mixed for 20 minutes. 0.364 g of Z6040 100% at 0.5% of solids was added and mixed for 20 minutes. 1.37 g of TYZOR La 100% at 1% of solids at 50% active was added and mixed for 20 minutes. 0.7 g of SUTTOCIDE A 100% at 0.5% of solids at 50% active was added and mixed for 20 minutes. 2.06 g of Propylene glycol 100% at 3% of volume was added and mixed for 20 minutes. 8.53 g of NALCO 1140 40% at 5% of solids was added and mixed for 20 minutes. 3.22 g of A196 100% at 0.4% of solids at 85% active was added and mixed for 20 minutes. 0.27 g of OT75 100% at 0.3% of solids at 75% active was added and mixed for 20 minutes. 0.14 g of SPAN80 100% at 0.2% of solids was added and mixed for 20 minutes. 82.7 g of A655, unmodified, at 45% of total volume was added and mixed for 15 minutes. 24.51 g of A621, unmodified, at 13.5% of total volume was added and mixed for 15 minutes. 35.56 g of A623, unmodified, at 19.4% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

SPECIFIC EXAMPLE 71

52 g of modified A630 and 52 g of modified A655 were mixed for 10 minutes. 38 g of modified A622 was added and mixed for 10 minutes. 30 g of modified A1054 was added and mixed for 10 minutes. 2.17 g of FC129 1% at 0.01 5% of solids at 50% active was added and mixed for 25 minutes. 1.02 g of L7602 10% at 0.14% of solids was added and mixed for 20 minutes. 0.364 g of Z6040 100% at 0.5% of solids was added and mixed for 20 minutes. 1.46 g of TYZOR La 100% at 1% of solids at 50% active was added and mixed for 20 minutes. 0.73 g of SUTTOCIDE A 100% at 0.5% of solids at 50% active was added and mixed for 20 minutes. 9.07 g of NALCO 1140 40% at 5% of solids was added and mixed for 20 minutes. 3.41 g of A196 100% at 0.4% of solids at 85% active was added and mixed for 20 minutes. 0.28 g of OT75 100% at 0.3% of solids at 75% active was added and mixed for 20 minutes. 0.147 g of SPAN80 100% at 0.2% of solids was added and mixed for 20 minutes. 43.42 g of A655, unmodified, at 23.6% of total volume was added and mixed for 15 minutes. 29.44 g of A630, unmodified, at 16.% of total volume was added and mixed for 15 minutes. 29.44 g of A623, unmodified, at 16% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

SPECIFIC EXAMPLE 72

52 g of modified A630 and 52 g of modified A655 were mixed for 10 minutes. 38 g of modified A622 was added and mixed for 10 minutes. 30 g of modified A1054 was added and mixed for 10 minutes. 2.17 g of FC129 1% at 0.01 5% of solids at 50% active was added and mixed for 25 minutes. 1.02 g of L7602 10% at 0.14% of solids was added and mixed for 20 minutes. 0.364 g of Z6040 100% at 0.5% of solids was added and mixed for 20 minutes. 1.46 g of TYZOR La 100% at 1% of solids at 50% active was added and mixed for 20 minutes. 0.73 g of SUTTOCIDE A 100% at 0.5% of solids at 50% active was added and mixed for 20 minutes. 9.07 g of NALCO 1140 40% at 5% of solids was added and mixed for 20 minutes. 3.41 g of A196 100% at 0.4% of solids at 85% active was added and mixed for 20 minutes. 0.28 g of OT75 100% at 0.3% of solids at 75% active was added and mixed for 20 minutes. 0.147 g of span80 100% at 0.2% of solids was added and mixed for 20 minutes. 67.68 g of A655, unmodified, at 36% of total volume was added and mixed for 15 minutes. 30.08 g of A630, unmodified, at 16.% of total volume was added and mixed for 15 minutes. 5 30.08 g of A623, unmodified, at 16.% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

SPECIFIC EXAMPLE 73

52 g of modified A630 and 52 g of modified A655 were mixed for 10 minutes. 38 g of modified A622 was added and mixed for 10 minutes. 30 g of modified A1054 was added and mixed for 10 minutes. 2.17 g of FC129 1% at 0.015% of solids at 50% active was added and mixed for 25 minutes. 1.02 g of L7602 10% at 0.14% of solids was added and mixed for 20 minutes. 0.364 g of Z6040 100% at 0.5% of solids was added and mixed for 20 minutes. 1.46 g of TYZOR La 100% at 1% of solids at 50% active was added and mixed for 20 minutes. 0.73 g of SUTTOCIDE A 100% at 0.5% of solids at 50% active was added and mixed for 20 minutes. 9.07 g of NALCO 1140 40% at 5% of solids was added and mixed for 20 minutes. 3.41 g of A196 100% at 0.4% of solids at 85% active was added and mixed for 20 minutes. 0.28 g of OT75 100% at 0.3% of solids at 75% active was added and mixed for 20 minutes. 0.147 g of SPAN80 100% at 0.2% of solids was added and mixed for 20 minutes. 78.426 g of A630, unmodified, at 41.72% of total volume was added and mixed for 15 minutes. 50.06 g of A633, unmodified, at 26.63% of total volume was added and mixed for 15 minutes. 51.17 g of A623, unmodified, at 27.22% of total volume was added and mixed for 15 minutes. Added nitocellulose solution at 0.125 g of total volume of solution, mixed 20 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

SPECIFIC EXAMPLE 74

52 g of modified A630 and 52 g of modified A655 were mixed for 10 minutes. 38 g of modified A622 was added and mixed for 10 minutes. 30 g of modified A1054 was added and mixed for 10 minutes. 2.17 g of FC129 1% at 0.015% of solids at 50% active was added and mixed for 25 minutes. 1.02 g of L7602 10% at 0.14% of solids was added and mixed for 20 minutes. 0.364 g of Z6040 100% at 0.5% of solids was added and mixed for 20 minutes. 1.46 g of TYZOR La 100% at 1% of solids at 50% active was added and mixed for 20 minutes. 0.73 g of SUTTOCIDE A 100% at 0.5% of solids at 50% active was added and mixed for 20 minutes. 9.07 g of NALCO 1140 40% at 5% of solids was added and mixed for 20 minutes. 3.41 g of A196 100% at 0.4% of solids at 85% active was added and mixed for 20 minutes. 0.28 g of OT75 100% at 0.3% of solids at 75% active was added and mixed for 20 minutes. 0.147 g of SPAN 80 100% at 0.2% of solids was added and mixed for 20 minutes. 94 g of JONCRYL 89, unmodified, at 50% of total volume was added and mixed for 15 minutes. 41.83 g of JONCRYL 77, unmodified, at 22.25% of total volume was added and mixed for 15 minutes. 45.12 g of BT44, unmodified, at 24% of total volume was added and mixed for 15 minutes. 18.91 g of N1140 40% at 5% of solids was added and mixed for 20 minutes. 0.756 g of Z6040 100% at 0.5% of solids was added and mixed for 20 minutes. 7.567 g of S104-PG 2% at 0.05% of solids at 50% active was added and mixed for 25 minutes. The amount of solvent (distilled water and ethanol, 100%), defoamer, germicide and thickener and pigment was based on 40% of solids.

SPECIFIC EXAMPLE 75

480 g of modified A622 and 288 g of modified A655 was mixed for 20 minutes. 160 g of modified A1054 was added and mixed for 20 minutes. 160 g of modified KRS2411 was added and mixed for 20 minutes. 16.04 g of S104E 10% at 0.0205% level of solids at 50% active was added and mixed for 30 minutes. 23.27 g of FC129 0.2% at 0.006% level of solids at 50% active was added and mixed for 30 minutes. 14.67 g of L7602 4% at 0.15% level of solids was added and mixed for 25 minutes. 2.51 g of Z6040 100% at 0.64% of solids was added and mixed for 25 minutes. 10.09 g of TYZOR LA 100% at 1.29% level of solids at 50% active was added and mixed for 25 minutes. 3.03 g of L7001 10% at 0.058% level of solids at 75% active was added and mixed for 25 minutes. 4.49 g of A196 10% at 0.068% level of solids at 85% active was added and mixed for 25 minutes. 3.92 g of N115 100% at 0.15% level of solids at 15% active was added and mixed for 25 minutes. 97.44 g of ethanol 200 proof was added and mixed for 25 minutes. SUTTOCIDE A was added in quantum sufficient. Thickeners were added in quantum sufficient. The amount of solvent, defoamer, germicide and thickener was based on 35.94% of solids.

SPECIFIC EXAMPLE 76

180 g of modified A622 and 108 g of modified A655 were mixed for 10 minutes. 60 g of modified A1054 was added and mixed for 10 minutes. 60 g of modified KRS2411 was added and mixed for 10 minutes. 5.78 g of L7602 4% at 0.15% of solids was added and mixed for 15 minutes. 4.62 g of SILWET 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

SPECIFIC EXAMPLE 77

180 g of modified A622 and 108 g of modified A655 were mixed for 10 minutes. 60 g of modified A1054 was added and mixed for 10 minutes. 72 g of modified KRS 2411 was added and mixed for 10 minutes. 6.07 g of L7602 4% at 0.15% of solids was added and mixed for 15 minutes. 6.63 g of S-104E 1% at 0.0205% of solids at 50% active was added and mixed for 25 minutes. 19.40 g of FC129 0.1% at 0.006% of solids at 50% active was added and mixed for 25 minutes. 4.62 g of Z6040 20% at 0.64% of solids was added and mixed for 15 minutes. 13.91 g of TYZOR LA 30% at 1.29% of solids at 50% active was added and mixed for 15 minutes. 12.51 g of L7001 1% at 0.058% of solids at 75% active was added and mixed for 15 minutes. 15.42 g of N1115 10% at 0.143% of solids at 15% active was added and mixed for 15 minutes. 12.37 g of A196 1% at 0.065% level of solids at 85% active was added and mixed for 15 minutes. The amount of solvent, defoamer, germicide and thickener was based on 38.50% of solids.

SPECIFIC EXAMPLE 78

180 g of modified A622 and 108 g of modified A655 were mixed for 10 minutes. 60 g of modified A1054 was added and mixed for 10 minutes. 72 g of modified KRS2411 was added and mixed for 10 minutes. 5.78 g of L7602 4% at 0.15% of solids was added and mixed for 15 minutes. 4.62 g of SILWET 77 1% at 0.03% of solids was added and mixed for 25 minutes. 5.18 g of Z6040 20% at 0.64% of solids was added and mixed for 15 minutes. 13.91 g of TYZOR LA 30% at 1.29% of solids at 50% active was added and mixed for 15 minutes. 5.14 g of N1115 10% at 0.05% of solids at 15% active was added and mixed for 15 minutes. The amount of solvent, defoamer, germicide and thickener was based on 38.50% of solids.

SPECIFIC EXAMPLE 79

360 g of modified A622 and 216 g of modified A655 were mixed for 20 minutes. 120 g of modified A1054 was added and mixed for 20 minutes. 60 g of modified KRS2411 was added and mixed for 20 minutes. 5.17 g of L7602 10% at 0.18% level of solids was added and mixed for 25 minutes. 8.62 g of S77 10% at 0.03% level of solids was added and mixed for 30 minutes. 0.96 g of N1115 100% at 0.05% level of solids at 15% active was added and mixed for 25 minutes. 2.3 g of Z6040 100% at 0.8% level of solids was added and mixed for 25 minutes. 9.19 g of TYZOR LA 100% at 1.6% level of solids at 50% active was added and mixed for 25 minutes. 22.98 g of propylene glycol 0.8% level of solids was added and mixed for 25 minutes. 2.87 g of SUTTOCIDE A 100% at 0.5% level of solids at 50% active was added and mixed for 25 minutes. The amount of solvent, defoamer, germicide and thickener was based on 38% of solids.

SPECIFIC EXAMPLE 80

180 g of modified A622 and 108 g of modified A655 were mixed for 20 minutes. 60 g of modified A1054 was added and mixed for 20 minutes. 2.38 g of L7602 10% at 0.18% of solids was added and mixed for 25 minutes. 3.97 g of S77 1% at 0.03% level of solids was added and mixed for 30 minutes. 0.44 g of N1115 100% at 0.05% level of solids at 15% active was added and mixed for 25 minutes. 30 g of modified KRS2411 was added and mixed for 20 minutes. 10.58 g of propylene glycol 100% at 0.8% level of solids was added and mixed for 25 minutes. 1.32 g of SUTTOCIDE A 100% at 0.5% level solids at 50% active was added and mixed for 25 minutes. The amount of solvent, defoamer, germicide and thickener was based on 38% of solids.

SPECIFIC EXAMPLE 81

180 g of modified A622 and 108 g of modified A655 were mixed for 20 minutes. 60 g of modified A1054 was added and mixed for 20 minutes. 30 g of modified KRS2411 was added and mixed for 20 minutes. 2.59 g of L7602 10% at 0.18% level of solids was added and mixed for 25 minutes. 4.31 g of S77 1% at 0.03% level of solids was added and mixed for 30 minutes. 0.48 g of N1115 100% at 0.05% level of solids at 15% active was added and mixed for 25 minutes. 11.49 g of propylene glycol at 0.8% level of solids was added and mixed for 25 minutes. 1.44 g of SUTTOCIDE A 100% at 0.5% level of solids at 50% active was added and mixed for 25 minutes. The amount of solvent, defoamer, germicide and thickener was based on 38% of solids.

SPECIFIC EXAMPLE 82

180 g of modified A622 and 108 g of modified A655 were mixed for 20 minutes. 1.97 g of L7602 10% at 0.18% level of solids was added and mixed for 25 minutes. 3.28 g of S77 1% at 0.03% level of solids was added and mixed for 30 minutes. 0.36 g of N1115 100% at 0.05% level of solids at 15% active was added and mixed for 25 minutes. 20 g of modified A1054 was added and mixed for 20 minutes. 0.88 g of Z6040 100% at 0.8% level of solids was added and mixed for 25 minutes. 3.5 g of TYZOR LA 100% at 1.6% level of solids at 50% active was added and mixed for 25 minutes. 8.76 g of propylene glycol 100% at 0.8% level of solids was added and mixed for 25 minutes. 1.09 g of SUTTOCIDE A 100% at 0.5% level of solids at 50% active was added and mixed for 25 minutes. The amount of solvent, defoamer, germicide and thickener was based on 38% of solids.

SPECIFIC EXAMPLE 83

180 g of modified A622 and 108 g of modified A655 were mixed for 20 minutes. 1.97 g of L7602 10% at 0.18% level of solids was added and mixed for 25 minutes. 3.28 g of S77 1% at 0.03% level of solids was added and mixed for 30 minutes. 0.36 g of N1115 100% at 0.05% level of solids at 15% active was added and mixed for 25 minutes. 60 g of modified A1054 was added and mixed for 20 minutes. 30 g of modified KRS2411 was added and mixed for 20 minutes. 0.88 g of Z6040 100% at 0.8% level of solids was added and mixed for 25 minutes. 3.5 g of TYZOR LA 100% at 1.6% level of solids at 50% active was added and mixed for 25 minutes. 8.76 g of propylene glycol 8% level of solids was added and mixed for 25 minutes. 1.09 g of SUTTOCIDE A 100% at 0.5% level of solids at 50% active was added and mixed for 25 minutes.

SPECIFIC EXAMPLE 84

180 g of modified A622 and 108 g of modified A655 were mixed for 10 minutes. 4.54 g of L7602 4% at 0.15% of solids was added and mixed for 15 minutes. 3.63 g of SILWET 77 1% at 0.03% of solids was added and mixed for 25 minutes. 4.03 g of N1115 10% at 0.05% of solids at 15% active was added and mixed for 15 minutes. The amount of solvent, defoamer, germicide and thickener was based on 38% of solids.

SPECIFIC EXAMPLE 85

180 g of modified A622 and 108 g of modified A655 were mixed for 10 minutes. 6.07 g of L7602 4% at 0.15% of solids was added and mixed for 15 minutes. 6.63 g of S-104E 1% at 0.0205% of solids at 50% active was added and mixed for 25 minutes. 19.40 g of FC129 1% at 0.006% of solids at 50% active was added and mixed for 25 minutes. 4.62 g of Z6040 20% at 0.64% of solids was added and mixed for 15 minutes. 13.91 g of TYZOR LA 30% at 1.29% of solids at 50% active was added and mixed for 15 minutes. 12.51 g of L7001 1% at 0.058% of solids at 75% active was added and mixed for 15 minutes. 15.42 g of N1115 10% at 0.143% of solids at 15% active was added and mixed for 15 minutes. 12.37 g of A196 1% at 0.065% of solids at 85% active was added and mixed for 15 minutes. The amount of solvent, defoamer, germicide and thickener was based on 38% of solids.

SPECIFIC EXAMPLE 86

180 g of modified A622 and 108 g of modified A655 were mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 1% at 0.006% of solids at 50% active was added and mixed for 25 minutes. 8.35 g of Z6040 20% at 0.64% of solids was added and mixed for 15 minutes. 22.45 g of TYZOR LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38% of solids.

The following are additional examples of the method of making the modified coatings:

SPECIFIC EXAMPLE 87

180 g of modified A622 and 108 g of modified A655 were mixed for 10 minutes. 60 g of modified A1054 was added and mixed for 10 minutes. 60 g of modified Z259 was added and mixed for 10 minutes. 5.78 g of L7602 4% at 0.15% of solids was added and mixed for 15 minutes. 4.62 g of SILWET 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

SPECIFIC EXAMPLE 88

180 g of modified A622 and 108 g of modified A655 were mixed for 10 minutes. 60 g of modified A1054 was added and mixed for 10 minutes. 60 g of modified C525 was added and mixed for 10 minutes. 5.78 g of L7602 4% at 0.15% of solids was added and mixed for 15 minutes. 4.62 g of SILWET 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

SPECIFIC EXAMPLE 89

180 g of modified A622 and 108 g of modified A655 were mixed for 10 minutes. 60 g of modified A1054 was added and mixed for 10 minutes. 60 g of modified BT44 was added and mixed for 10 minutes. 5.78 g of L7602 4% at 0.15% of solids was added and mixed for 15 minutes. 4.62 g of SILWET 77 1% at 0.03% of solids was added and mixed for 25 minutes. 5.14 g of N1115 10% at 0.05% of solids at 15% active was added and mixed for 15 minutes. The amount of solvent, defoamer, germicide and thickener was based on 37.75% of solids.

SPECIFIC EXAMPLE 90

180 g of modified A622 and 108 g of modified A655 were mixed together for 10 minutes. 120 g of modified A1054 was added and mixed for 10 minutes. 90 g of modified KRS2411 was added and mixed for 10 minutes. 90 g of modified BT44 was added and mixed for 10 minutes. 90 g of modified Z259 was added and mixed for 10 minutes. 90 g of modified C525 was added and mixed for 10 minutes. 16.06 g of DF75 10% at 0.5435% of solids was added and mixed for 15 minutes. 12.13 g of S-104E 1% at 0.0205% of solids at 50% active was added and mixed for 25 minutes. 35.48 g of FC129 0.1% at 0.006% of solids at 50% active was added and mixed for 25 minutes. 9.46 g of Z6040 20% at 0.64% of solids was added and mixed for 15 minutes. 25.43 g of TYZOR LA 30% at 1.29% of solids at 50% active was added and mixed for 15 minutes. 22.87 of L7001 1% at 0.058% of solids at 75% active was added and mixed for 15 minutes. 28.19 g of N1115 10% at 0.143% of solids at 15% active was added and mixed for 15 minutes. 22.61 g of A196 1% at 0.065% of solids at 85% active was added and mixed for 15 minutes. The amount of solvent, defoamer, germicide and thickener was based on 38.50% of solids.

SPECIFIC EXAMPLE 91

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified BT44 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of TYZOR LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

SPECIFIC EXAMPLE 92

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of TYZOR LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

SPECIFIC EXAMPLE 93

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 0.15% of solids was added and mixed for 15 minutes. 7.83 g of SILWET 77 1% at 0.03% of solids was added and mixed for 25 minutes. 8.35 g of Z6040 20% at 0.64% of solids was added and mixed for 15 minutes. 22.45 g of TYZOR LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

SPECIFIC EXAMPLE 94

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 0.15% of solids was added and mixed for 15 minutes. 10.71 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of TYZOR LA 30% at 1.29% of solids at 50% active was added and mixed for 15 minutes. 20.19 g of L7001 1% at 0.058% of solids at 75% active was added and mixed for 15 minutes. 26.11 g of N1115 10% at 0.15% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

SPECIFIC EXAMPLE 95

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 9.79 g of L7602 4% at 15% of solids was added and mixed for 15 minutes. 7.83 g of SILWET 77 1% at 0.03% of solids was added and mixed for 25 minutes. 8.35 g of Z6040 20% at 0.64% of solids was added and mixed for 15 minutes. 22.45 g of TYZOR LA 30% at 1.29% of solids at 50% active was added and mixed for 15 minutes. 26.03 g of N1115 10% at 0.15% of solids at 15% active was added and mixed for 15 minutes. The amount of solvent, defoamer, germicide and thickener was based on 38.50% of solids.

SPECIFIC EXAMPLE 96

180 g of modified A622 and 108 g of modified A655 were mixed for 10 minutes. 120 g of modified A1054 was added and mixed for 10 minutes. 90 g of modified KRS2411 was added and mixed for 10 minutes. 90 g of modified Z259 was added and mixed for 10 minutes. 90 g of modified C525 was added and mixed for 10 minutes. 14.18 g of DF75 1% at 0.5435% of solids was added and mixed for 15 minutes. 10.70 g of S-104E 1% at 0.0205% of solids at 50% active was added and mixed for 25 minutes. 31.33 g of FC129 0.1% at 0.006% of solids at 50% active was added and mixed for 25 minutes. 8.35 g of Z6040 20% at 0.64% of solids was added and mixed for 15 minutes 22.45 g of TYZOR LA 30% at 1.29% of solids at 50% active was added and mixed for 15 minutes. 20.19 g of L7001 1% at 0.058% of solids at 75% active was added and mixed for 15 minutes. 24.89 g of N1115 10% at 0.143% of solids at 15% active was added and mixed for 15 minutes. 19.96 g of A196 1% at 0.065% of solids at 85% active was added and mixed for 15 minutes. The amount of solvent, defoamer, germicide and thickener was based on 38.50% of solids.

IV. Pigmented Coatings

Pigmented coatings are obtained by adding dispersed treated pigments to the cellulose-based coatings. The dispersed treated pigments are obtained by repeatedly mixing the pigments with silanes, titanates and other additives, and heating until desiccation. Distilled water may be added at each step to allow for proper mixing. The treated pigments are then milled with a wetting agent and dispersing surfactant. The milled pigment is added to the appropriate coating formula.

Generally, the pigments are placed in a glass beaker and silane is added. Pigments employed in the present invention include but are not limited to D & C red 21, D & C yellow, D & C cosmetic iron blue, D & C T102 and D & C cosmetic dioxide. Silanes used in the present invention include but are not limited to Z 6040, 25-additive, A 1100, and Z 6020. After mixing the pigments and silane for about 5 minutes, the vessel is heated with occassional stirring until all the liquid is desiccated. Titanate is then added and the mass is mixed for about 5 minutes. The titanates employed in the present invention include TYZOR TE, and TYZOR LA. The mass is then heated with occassional stirring until all the liquid has dried. Again, silane is added and the mass is mixed for about 5 minutes. The mass is heated and stirred until desiccated. Silane is added and mixed for about 5 minutes. The mass is again heated and stirred until desiccated. The material is placed in a mill, then dispersed with a wetting agent for about 30 minutes. The preferred wetting agent of the present invention is S-104E but others known in the art may be employed. Finally, a dispersing surfactant is added and the material is placed in a mill for about 90 minutes. The preferred dispersing surfactants of the present invention are CT 136 and L7602. The dispersed treated pigments are then added to the coating prepared as described above and mixed for about 20 minutes. The following examples employ the general technique described above to formulate the dispersed treated pigments:

SPECIFIC EXAMPLE 97

0.55 g D&C red 6, 0.45 g D&C red 34 and 1 g Z6040 (10%) at 10% of solids were combined in a glass beaker, mixed for 5 minutes and microwaved at high for 5 minutes. 4 g TYZOR TE (10%) at 26% of solids at 50% active was added, mixed for 5 minutes and microwaved for 5 minutes at high. 5 g of distilled water was added. 0.5 g of CMC-7H (1%) at 0.0625% level of solids was added and mixed for 5 minutes and microwaved for 5 minutes at high.

SPECIFIC EXAMPLE 98

12 g D&C red 6 and 24 g Z 6040 (10%) at 20% of solids were combined in a glass beaker, mixed for 20 minutes and microwaved at high for 10 minutes. 24 g of TYZOR TE (10%) at 10% of solids at 50% active was added. 60 g of distilled water was added. The combination was mixed for 5 minutes and microwaved at high for 10 minutes. 6 g of CMC-7H (1%) at 0.5% of solids was added and mixed for 5 minutes and microwaved for 5 minutes at high.

SPECIFIC EXAMPLE 99

14 g of D&C red 6 and 14 g of Z 6040 (10%) at 10% of solids were combined in a glass beaker, mixed for 5 minutes and microwaved at high for 10 minutes. 28 g of TYZOR LA (10%) at 10% of solids at 50% active was added. The combination was mixed for 5 minutes and microwaved at high for 10 minutes. 14 g of Z 6020 (10%) at 10% of solids was added, mixed for 5 minutes and microwaved at high for 10 minutes. 7 g of CMC-7H (1%) at 0.5% solids was mixed for 5 minutes and microwaved for 10 minutes at high.

SPECIFIC EXAMPLE 100

14 g of D&C red 6 and 14 g of Z 6040 (10%) at 10% of solids were combined in a glass beaker, mixed for 5 minutes and microwaved at high for 10 minutes. 28 g of TYZOR LA (10%) at 10% of solids at 50% active was added. The combination was mixed for 5 minutes and then microwaved at high for 10 minutes. 14 g of Z 6020 (10%) at 10% of solids was added, mixed for 5 minutes and microwaved at high for 10 minutes. 14 g of A 1100 (10%) at 10% of solids was added, mixed for 5 minutes and microwaved at high for 10 minutes. 7 g of CMC-7H (1%) at 0.5% solids was added, mixed for 5 minutes and microwaved for 10 minutes at high.

SPECIFIC EXAMPLE 101

4.02 g of D&C red 7, 0.8 g of D&C red 6, 1.8 g of D & C $TiO_2$, 3.13 g of D&C red 34, 0.01 g of D&C cosmetic iron blue, 0.25 g of D&C yellow 5 and 0.02 g of D&C cosmetic dioxide (total of 10 g of pigment) and 10 g of Z 6040 (10%) at 10% of solids were combined in a glass beaker, mixed for 5 minutes and microwaved at high for 10 minutes. 30 g of TYZOR LA (10%) at 15% of solids at 50% active was added. The combination was mixed for 5 minutes and microwaved at high for 10 minutes. 10 g of Z 6020 (10%) at 10% of solids was added, mixed for 5 minutes and microwaved at high for 10 minutes. 10 g of A 1100 (10%) at 10% of solids was added, mixed for 5 minutes and microwaved at high for 10 minutes. 5 g of CMC-7H (1%) at 0.5% of solids was added and mixed for 5 minutes and microwaved for 5 minutes at high. 6.67 g of NALCO 1115 100% at 10% of solids at 15% active and 10 g of distilled water were added, mixed for 5 minutes and microwaved at high for 5 minutes.

SPECIFIC EXAMPLE 102

4.02 g of D&C red 7, 0.8 g of D&C red 6, 1.8 g of D&C $TiO_2$, 3.13 g of D&C red 34, 0.01 g of D&C cosmetic iron blue, 0.25 g of D&C yellow 5, 0.02 of D&C cosmetic dioxide (total of 10 g of pigment) and 10 g of Z 6040 (10%) at 10% of solids were combined in a glass beaker, mixed for 5 minutes and microwaved at high for 10 minutes. 30 g of TYZOR LA (10%) at 15% of solids at 50% active was added. The combination was mixed for 5 minutes and microwaved at high for 10 minutes. 10 g of Z 6020 (10%) at 10% of solids was added, mixed for 5 minutes and microwaved at high for 10 minutes. 10 g of A 1100 (10%) at 10% of solids was added, mixed for 5 minutes and microwaved at high for 10 minutes. 50 g of CMC-7H (1%) at 5% of solids was added and mixed for 5 minutes and microwaved for 5 minutes at high.

SPECIFIC EXAMPLE 103

4.02 g of D&C red 7, 0.08 of D&C red 6, 1.8 g of D&C $TiO_2$, 3.13 g of D&C red 34, 0.01 g of D&C cosmetic iron blue, 0.25 g of D&C yellow 5, 0.02 g of D&C cosmetic dioxide (total of 10 g of pigment) and 20 g of Z 6040 (10%) of 20% of solids were combined in a glass beaker, mixed for 10 minutes and microwaved at high for 5 minutes. 80 g of TYZOR LA (10%) at 40% of solids at 50% active was added. The combination was mixed for 5 minutes and microwaved at high for 10 minutes. 20 g of Z 6020 (10%) at 20% of solids was added, mixed for 5 minutes and microwaved at high for 10 minutes. 20 g of A 1100 (10%) at 20% of solids was added, mixed for 5 minutes and microwaved at high for 10 minutes.

SPECIFIC EXAMPLE 104

10 g of pigment, 5 g of Z6040 20% at 10% level of solids and 10 g of distilled water were combined in a glass beaker, mixed for 5 minutes and microwaved for 4 minutes at high. 20 g of TYZOR LA or TYZOR TE 30% at 30% of solids at 50% active, 1 g of 25-additive 100% at 10% of solids, 5 g of Z6020 20% at 10% level of solids and 10 g of distilled water were combined and added to the above mixture. The mixture was then mixed for 5 minutes and microwaved for 4 minutes at high. 5 g of A1100 20% at 10% level of solids and 10 g of distilled water were combined and added to the above mixture. The mixture was then mixed for 5 minutes and microwaved for 4 minutes at high. 30 g of CMC-7H 1% at 3% of solids was then mixed for 5 minutes and microwaved for 4 minutes at high. 20 g of NALCO 1115 100% at 30% of solids at 15% active and 10 g of distilled water were combined and added to the above mixture. The mixture was then mixed for 5 minutes and microwaved at high for 4 minutes.

SPECIFIC EXAMPLE 105

10 g of pigment, 10 g of Z6040 20% at 20% level of solids and 10 g of distilled water were combined in a glass beaker, mixed for 5 minutes and microwaved for 4 minutes at high. 33.3 g of TYZOR LA or TYZOR TE 30% at 50% of solids at 50% active, 2 g of 25-additive 100% at 20% of solids, 10 g of Z6020 20% at 20% level of solids and 10 g of distilled water were combined and added to the above mixture. The mixture was then mixed for 5 minutes and microwaved for 4 minutes at high. 10 g of A1100 20% at 20% level of solids and 10 g of distilled water were combined and added to the above mixture. The mixture was then mixed for 5 minutes and microwaved for 4 minutes at high. 40 g of CMC-7H 1% at 4% of solids was then mixed for 5 minutes and microwaved for 4 minutes at high. 26.67 g of NALCO 1115 100% at 40% of solids at 15% active and 10 g of distilled water were combined and added to the above mixture. The mixture was then mixed for 5 minutes and microwaved at high for 4 minutes.

SPECIFIC EXAMPLE 106

10 g of pigment, 15 g of Z6040 20% at 30% level of solids and 10 g of distilled water were combined in a glass beaker, mixed for 5 minutes and microwaved for 4 minutes at high.

40 g of TYZOR LA or TYZOR TE 30% at 60% of solids at 50% active, 5 g of 25-additive 100% at 50% of solids, 20 g of Z6020 20% at 40% level of solids and 10 g of distilled water were combined and added to the above mixture. The mixture was then mixed for 5 minutes and microwaved for 4 minutes at high. 20 g of A1100 20% at 40% level of solids and 10 g of distilled water were combined and added to the above mixture. The mixture was then mixed for 5 minutes and microwaved for 4 minutes at high. 10 g of CMC-7H 1% at 1% of solids was then mixed for 5 minutes and microwaved for 4 minutes at high. 10 g of NALCO 1115 100% at 15% of solids at 15% active and 10 g of distilled water were combined and added to the above mixture. The mixture was then mixed for 5 minutes and microwaved at high for 4 minutes.

SPECIFIC EXAMPLE 107

10 g of pigment, 20 g of Z6040 20% at 40% level of solids and 10 g of distilled water were combined in a glass beaker, mixed for 5 minutes and microwaved for 4 minutes at high. 46.67 g of TYZOR LA or TYZOR TE 30% at 70% of solids at 50% active, 6 g of 25-additive 100% at 60% of solids, 20 g of Z6020 20% at 40% level of solids and 10 g of distilled water were combined and added to the above mixture. The mixture was then mixed for 5 minutes and microwaved for 4 minutes at high. 20 g of A1100 20% at 40% level of solids and 10 g of distilled water were combined and added to the above mixture. The mixture was then mixed for 5 minutes and microwaved for 4 minutes at high. 50 g of CMC-7H 1% at 5% of solids was then mixed for 5 minutes and microwaved for 4 minutes at high. 36.67 g of NALCO 1115 100% at 55% of solids at 15% active and 10 g of distilled water were combined and added to the above mixture. The mixture was then mixed for 5 minutes and microwaved at high for 4 minutes.

The following examples employ the most preferred method of formulating the pigmented coatings:

SPECIFIC EXAMPLE 108

The coating is prepared by the following method.

60 g of modified A630 and 60 g of modified A655 were mixed for 10 minutes. 40 g of modified A622 was added and mixed for 10 minutes. 20 g of modified A1054 was added and mixed for 10 minutes. 0.44 g of FC129 5% at 0.01 5% of solids at 50% active was added and mixed for 25 minutes. 2.04 g of L7602 5% at 0.14% of solids was added and mixed for 20 minutes. 0.364 g of Z6040 100% at 0.5% of solids was added and mixed for 20 minutes. 1.45 g of TYZOR La 100% at 1% of solids at 50% active was added and mixed for 20 minutes. 0.73 g of SUTTOCIDE A 100% at 0.5% of solids at 50% active was added and mixed for 20 minutes. 9.09 g of NALCO 1140 40% at 5% of solids was added and mixed for 20 minutes. 3.42 g of A196 100% at 0.4% of solids at 85% active was added and mixed for 20 minutes. 0.29 g of OT75 100% at 0.3% of solids at 75% active was added and mixed for 20 minutes. 0.15 g of SPAN 80 100% at 0.2% of solids was added and mixed for 20 minutes. 63.95 g of A630, unmodified, at 31.5% of total volume was added and mixed for 15 minutes. 19.61 g of A633, unmodified, at 9.66% of total volume was added and mixed for 15 minutes. 28.28 g of A645, unmodified, at 20% of total volume was added and mixed for 15 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids, as required.

The pigments are treated by the following technique.

10 g of Red 27 Alumina Lake/TiO$_2$/Zirconium lake, 2 g of Z6040 100% at 20% level of solids, 20 g of distilled water and the pigment were mixed for 5 minutes and heated until dessicated while mixing. 8.08 g of TYZOR LA 100% at 40% level of solids at 50% active and 20 g of distilled water were added, mixed for 5 minutes and heated until dessicated while mixing. 2 g of Z6020 20% at 100% level of solids and 20 g of distilled water was added, mixed for 5 minutes and heated until dessicated while mixing. 2 g of A1100 100% at 20% level of solids and 20 g of distilled water was added, mixed for 5 minutes and heated until dessicated while mixing. 10 g of CMC-7H 1% at 1% level of solids and 20 g of distilled was added, mixed for 5 minutes and heated until dessicated while mixing. 5 g of N1140 40% at 20% level of solids and 20 g of distilled water were added, mixed for 5 minutes and heated until dessicated while mixing.

4 g of the above treated pigments was added to a plastic container with metal balls. 4 g of S104PG 2% at 1% level of solids at 50% active was added with 2 g ethanol 10% at 5% level and 2 g distilled water at 5% of solids. This was milled for 30 minutes. 11.2 g of L7602 5% at 14% level of solids was added and milled for 120 minutes.

The above coating was added at 3 g of pigment to 100 g of coating.

SPECIFIC EXAMPLE 109

The coating is prepared by the following method.

360 g of modified A622 and 216 g of modified A655 were mixed for 20 minutes. 120 g of modified A1054 was added and mixed for 25 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 15.76 g of propylene glycol at 8% level were added and mixed for 25 minutes. 2.18 g of SUTTOCIDE A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

The pigments are treated by the following technique.

6 g of Ba lake #6 red, 2 g of Orange #5 AL lake, 2 g of red #34 Ca lake and 10 g of red #7 Ca lake were combined (20 g of pigment). 20 g of Z6040 20% at 20% level of solids, 10 g of distilled water and the pigment were mixed for 5 minutes and microwaved for 6 minutes at high. 16.08 g of TYZOR LA 100% at 40% level of solids at 50% active and log of distilled water were added, mixed for 5 minutes and microwaved for 6 minutes at high. 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40.2 g of CMC-7H 1% at 2% level of solids was added, mixed for 10 minutes and microwaved for 6 minutes at high. 40 g of N1115 100% at 30% level of solids at 15% active and 20 g of distilled water were added, mixed for 10 minutes and microwaved for 6 minutes at high. 8 g of the above treated pigments was added to a metal cylinder with metal balls. 8 g of SILWET 77 1% at 1% level of solids was added and milled for 60 minutes. 1.44 g of L7602 100% at 18% level of solids was added and milled for 120 minutes.

The treated pigments from above are dispersed by the following technique.

8 g of treated pigment and 4 g of CMC-7H 10% at 0.5% level of solids were mixed and milled for 15 minutes. 8 g of S104E 2% at 1% level of solids at 50% active was added and milled for 30 minutes. 1.44 g of L7602 100% at 18% level of solids was added and milled for 90 minutes. The coating from above was added in quantum sufficient for desired intensity of color.

The following examples employ a preferred method of formulating the pigmented coatings:

SPECIFIC EXAMPLE 110

52 g of modified A630 and 52 g of modified A655 were mixed for 10 minutes. 38 g of modified A622 was added and mixed for 10 minutes. 30 g of modified A1054 was added and mixed for 10 minutes. 2.17 g of FC129 1% at 0.015% of solids at 50% active was added and mixed for 25 minutes. 1.02 g of L7602 10% at 0.14% of solids was added and mixed for 20 minutes. 0.364 g of Z6040 100% at 0.5% of solids was added and mixed for 20 minutes. 1.46 g of TYZOR La 100% at 1% of solids at 50% active was added and mixed for 20 minutes. 0.73 g of SUTTOCIDE A 100% at 0.5% of solids at 50% active was added and mixed for 20 minutes. 9.07 g of NALCO 1140 40% at 5% of solids was added and mixed for 20 minutes. 3.41 g of A196 100% at 0.4% of solids at 85% active was added and mixed for 20 minutes. 0.28 g of OT75 100% at 0.3% of solids at 75% active was added and mixed for 20 minutes. 0.147 g of SPAN 80 100% at 0.2% of solids was added and mixed for 20 minutes. 78.426 g of A630, unmodified, at 41.72% of total volume was added and mixed for 15 minutes. 50.06 g of A633, unmodified, at 26.63% of total volume was added and mixed for 15 minutes. 51.17 g of A623, unmodified at 27.22% of total volume was added and mixed for 15 minutes. Added nitocellulose solution at 0.125 g of total volume of solution, mixed 20 minutes. 0.7 g of S104-PG 2% at 0.03% of solids at 50% active was added and mixed for 25 minutes. The amount of solvent (distilled water and ethanol, 100%), defoamer, germicide and thickener and pigment was based on 40% of solids.

The pigments are treated by the following technique.

10 g of Red 27 Alumina Lake/TiO$_2$/Zirconium lake. 2 g of Z6040 100% at 20% level of solids, 20 g of distilled water and the pigment were mixed for 5 minutes and heated until dessicated while mixing. 8.08 g of TYZOR LA 100% at 40% level of solids at 50% active and 20 g of distilled water were added, mixed for 5 minutes and heated until dessicated while mixing. 2 g of Z6020 20% at 100% level of solids and 20 g of distilled water was added, mixed for 5 minutes and heated until dessicated while mixing. 2 g of A1100 100% at 20% level of solids and 20 g of distilled water was added, mixed for 5 minutes and heated until dessicated while mixing. 20 g of CMC-7H 1% at 2% level of solids and 20 g of distilled was added, mixed for 5 minutes and heated until dessicated while mixing. 5 g of N1140 40% at 20% level of solids and 20 g of distilled water were added, mixed for 5 minutes and heated until dessicated while mixing.

4 g of the above treated pigments was added to a plastic container with metal balls. 4 g of S104PG 2% at 1% level of solids at 50% active was added with 2 g ethanol 10% at 5% level and 2 g distilled water at 5% of solids. This was milled for 30 minutes. 11.2 g of L7602 5% at 14% level of solids was added and milled for 120 minutes.

The above coating was added at 3 g of pigment to 100 g of coating.

SPECIFIC EXAMPLE 111

The coating is prepared by the following method.

360 g of modified A622 and 216 g of modified A655 were mixed for 20 minutes. 120 g of modified A1054 was added and mixed for 25 minutes. 120 g of modified R960 was added and mixed for 25 minutes. 8.154 g of L7602 4% at 0.15% level of solids was added and mixed for 25 minutes. 6.53 g of S-77 1% at 0.03% level of solids was added and mixed for 30 minutes. 0.75 g of N1115 100% at 0.05% level of solids at 15% active was added and mixed for 25 minutes. 15.76 g of propylene glycol at 8% level were added and mixed for 25 minutes. 2.18 g of SUTTOCIDE A 100% at 0.5% level of solids at 50% active was added and mixed for 25 minutes. Thickener was added in quantum sufficient, 0.2% to 0.8% of total solids. The amount of solvent, defoamer, germicide and thickener was based on 37.75% of solids.

The pigments are treated by the following technique.

6 g of Ba lake #6 red, 2 g of Orange #5 AL lake, 2 g of red #34 Ca lake and 10 g of red #7 Ca lake were combined (20 g of pigment). 20 g of Z6040 20% at 20% level of solids, 10 g of distilled water and the pigment were mixed for 5 minutes and microwaved for 6 minutes at high. 16.08 g of TYZOR LA 100% at 40% level of solids at 50% active and 10 g of distilled water were added, mixed for 5 minutes and microwaved for 6 minutes at high. 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40.2 g of CMC-7H 1% at 2% level of solids was added, mixed for 10 minutes and microwaved for 6 minutes at high. 40 g of N1115 100% at 30% level of solids at 15% active and 20 g of distilled water were added, mixed for 10 minutes and microwaved for 6 minutes at high. 8 g of the above treated pigments was added to a metal cylinder with metal balls. 8 g of 77 SILWET. 1% at 1% level of solids was added and milled for 60 minutes. 1.44 g of L7602 100% at 18% level of solids was added and milled for 120 minutes.

The treated pigments from above are dispersed by the following technique.

8 g of treated pigment and 4 g of CMC-7H 10% at 0.5% level of solids were mixed and milled for 15 minutes. 8 g of S104E 2% at 1% level of solids at 50% active was added and milled for 30 minutes. 1.44 g of L7602 100% at 18% level of solids was added and milled for 90 minutes. The coating from above was added in quantum sufficient for desired intensity of color.

SPECIFIC EXAMPLE 112

The coating is prepared by the following method.

480 g of modified A622 and 288 g of modified A655 were mixed for 20 minutes. 160 g of modified A1054 was added and mixed for 20 minutes. 160 g of modified KRS2411 was added and mixed for 20 minutes. 16.04 g of S104E 10% at 0.0205% level of solids at 50% active was added and mixed for 30 minutes. 23.27 g of FC129 0.2% at 0.006% level of solids at 50% active was added and mixed for 30 minutes. 14.67 g of L7602 4% at 0.15% level of solids was added and mixed for 25 minutes. 2.51 g of Z6040 100% at 0.64% of solids was added and mixed for 25 minutes. 10.09 g of TYZOR LA 100% at 1.29% level of solids at 50% active was added and mixed for 25 minutes. 3.03 g of L7001 10% at 0.058% level of solids at 75% active was added and mixed for 25 minutes. 4.49 g of A196 10% at 0.068% level of solids at 85% active was added and mixed for 25 minutes. 3.92 g of N 115 100% at 0.15% level of solids at 15% active was added and mixed for 25 minutes. 97.44 g of ethanol 200 proof was added and mixed for 25 minutes. SUTTOCIDE A was added in quantum sufficient. Thickeners were added in quantum sufficient.

The pigments are treated by the following technique.

20 g of pigment, 20 g of Z6040 20% at 20% level of solids and 10 g of distilled water were mixed for 5 minutes and microwaved for 6 minutes at high. 40 g of TYZOR LA 40% at 40% level of solids at 50% active was added, mixed for 5 minutes and microwaved for 6 minutes at high. 6 g of #25 (Dow Corning) at 100% at 30% level of solids, 20 g of Z6020 20% at 20% level of solids and 10 g of distilled water was added, mixed for 5 minutes and microwaved for 6 minutes at high. 20 g of A1100 20% at 20% level of solids and 10 g of distilled water was added, mixed for 5 minutes and microwaved for 6 minutes at high. 40 g of CMC-7H 1% at 20% level of solids and 20 g of distilled water were added, mixed for 5 minutes and microwaved for 6 minutes at high. 40 g of N1115 100% at 30% level of solids at 15% active was added, mixed for 5 minutes and microwaved for 6 minutes at high.

The treated pigments from above are dispersed by the following technique.

5 g of treated pigment, 5 g of SILWET 77 1% at 1% level of solids, and 20 g of distilled water were placed in a shaker and were shaken for 60 minutes. 0.9 g of L7602 100% at 18% level of solids was added and shaken for 120 minutes. The treated and dispersed pigments were then added to 120 g of the above coating.

What is claimed is:

1. A method for preparing an aqueous cellulose composition comprising the following steps:
   a) mixing water and a cellulose compound selected from the group consisting of nitrocellulose, ethylcellulose and cellulose acetate butyrate in a ratio of from about 2 parts by weight water per part by weight cellulose compound to about 20 parts by weight water per part by weight cellulose compound, thereby forming a water-cellulose mixture;
   b) adding a glycol ether solvent to the water-cellulose mixture in a ratio of from about 2 parts by weight solvent to about 20 parts by weight solvent per part by weight cellulose compound present in the water-cellulose mixture thereby forming a water-cellulose solvent mixture; and
   c) mixing the water-cellulose solvent mixture thereby forming an aqueous cellulose solution.

2. The method of claim 1 wherein the step of mixing water and a cellulose compound further comprises adding the water to the cellulose compound in multiple steps.

3. An aqueous nitrocellulose solution obtained by the method of claim 1.

4. An aqueous ethylcellulose solution obtained by the method of claim 1.

5. An aqueous cellulose acetate butyrate solution obtained by the method of claim 1.

6. An aqueous cellulose solution consisting essentially of a cellulose compound selected from the group consisting of nitrocellulose, ethylcellulose and cellulose acetate butyrate, water and glycol ether solvent in a ratio of from about 2 to about 20 parts by weight water and from about 2 to about 20 parts by weight solvent, per part by weight cellulose compound.

7. An aqueous cellulose solution consisting essentially of a cellulose compound selected from the group of nitrocellulose, ethylcellulose and cellulose acetate butyrate, water and glycol ether solvent in a ratio of from about 0.5 to about 4 parts by weight water and from about 1 to about 7 parts by weight solvent, per part by weight cellulose compound.

8. An aqueous cellulose solution comprising a cellulose compound selected from the group consisting of nitrocellulose, ethylcellulose and cellulose acetate butyrate, water and glycol ether solvent in a ratio of from about 2 to about 20 parts by weight water and from about 2 to about 20 parts by weight solvent, per part by weight cellulose compound.

9. An aqueous cellulose solution comprising a cellulose compound selected from the group of nitrocellulose, ethylcellulose and cellulose acetate butyrate, water and glycol ether solvent in a ratio of from about 0.5 to about 4 parts by weight water and from about 1 to about 7 parts by weight solvent, per part by weight cellulose compound.

* * * * *